US011072795B2

(12) United States Patent
Surana et al.

(10) Patent No.: US 11,072,795 B2
(45) Date of Patent: Jul. 27, 2021

(54) ANTISENSE OLIGONUCLEOTIDES

(71) Applicant: AGENCY FOR SCIENCE, TECHNOLOGY AND RESEARCH, Singapore (SG)

(72) Inventors: Uttam Surana, Singapore (SG); Dave Keng Boon Wee, Singapore (SG); Jing Lin, Singapore (SG); Bing Lim, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 16/345,487

(22) PCT Filed: Oct. 16, 2017

(86) PCT No.: PCT/SG2017/050517
§ 371 (c)(1),
(2) Date: Apr. 26, 2019

(87) PCT Pub. No.: WO2018/080393
PCT Pub. Date: May 3, 2018

(65) Prior Publication Data
US 2019/0309302 A1    Oct. 10, 2019

(30) Foreign Application Priority Data
Oct. 28, 2016  (SG) ........................... 10201609048R

(51) Int. Cl.
| C12N 15/11 | (2006.01) |
| C12N 15/113 | (2010.01) |
| A61P 35/00 | (2006.01) |
| A61K 9/00 | (2006.01) |
| A61K 31/7088 | (2006.01) |
| A61K 45/06 | (2006.01) |
| C12Q 1/6886 | (2018.01) |
| A61K 31/7125 | (2006.01) |
| A61K 31/712 | (2006.01) |

(52) U.S. Cl.
CPC ........ *C12N 15/1137* (2013.01); *A61K 9/0029* (2013.01); *A61K 31/7088* (2013.01); *A61K 31/712* (2013.01); *A61K 31/7125* (2013.01); *A61K 45/06* (2013.01); *A61P 35/00* (2018.01); *C12Q 1/6886* (2013.01); *C12N 2310/11* (2013.01); *C12N 2310/315* (2013.01); *C12N 2310/321* (2013.01); *C12N 2310/3233* (2013.01); *C12N 2310/346* (2013.01); *C12N 2310/351* (2013.01); *C12N 2320/32* (2013.01); *C12N 2320/33* (2013.01)

(58) Field of Classification Search
CPC ... A61P 35/00; C12Q 1/6886; C12N 2310/11; C12N 2310/315; C12N 2310/321; C12N 2310/351
See application file for complete search history.

(56) References Cited

U.S. PATENT DOCUMENTS

| 7,608,413 B1 * | 10/2009 | Joseloff | C12Q 1/6886 435/7.23 |
| 2006/0134663 A1 * | 6/2006 | Harkin | C12Q 1/6837 435/6.11 |
| 2007/0037165 A1 * | 2/2007 | Venter | C12Q 1/6883 435/6.11 |
| 2013/0296188 A1 | 11/2013 | Lim et al. | |

FOREIGN PATENT DOCUMENTS

| WO | 2011057350 A1 | 5/2011 |
| WO | 2013120086 A1 | 8/2013 |

OTHER PUBLICATIONS

Chen et al, Identifying the novel key genes in renal cell carcinoma by bioinformatics analysis and cell experiments, Cancer Cell International, 2020, pp. 1-26 (Year: 2020).*
Communication (International Preliminary Report on Patentability) issued by the International Searching Authority in Application No. PCT/SG2017/050517 dated Aug. 20, 2018, 20 pages total. International.
Communication (International Search Report and Written Opinion) issued by the International Searching Authority in International Application No. PCT/SG2017/050517 dated Dec. 11, 2017, 5 pages total.
Dias, N. et al., "Antisense Oligonucleotides: Basic Concepts and Mechanisms" Molecular Cancer Therapeutics (2002) vol. 1, pp. 347-355.
Chan, J.HP et al., "Antisense Oligonucleotides: From Design to Therapeutic Application" Clinical and Experimental Pharmacology and Physiology (2006) vol. 33, pp. 533-540.
Zhang, W C et al., "Abstract 1438: Targeting Metabolic Enzyme with Locked Nucleic Acids in Non-Small Cell Lung Cancer" Molecular and Cellular Biology (2014) Proceedings of the 105th Annual Meeting of the American Association for Cancer Research, vol. 74, Supplemental 19, Abstract.

(Continued)

*Primary Examiner* — Ekaterina Poliakova-Georgantas
(74) *Attorney, Agent, or Firm* — Troutman Pepper Hamilton Sanders LLP

(57) ABSTRACT

The present invention relates to antisense oligonucleotides for modulating the activity of glycine decarboxylase (GLDC). In particular, the present invention relates to antisense oligonucleotides capable of inducing exon skipping of RNA. Also claimed are pharmaceutical compositions, kits and methods of treating cancer and inducing exon-skipping using said antisense oligonucleotides. In addition, a method for aiding the categorising or determining prognosis of a cancer or in selecting a therapeutic strategy for a patient with cancer, based on assessing the level of GLDC nucleic acid, protein or activity in a sample derived from the patient is provided.

8 Claims, 7 Drawing Sheets
(6 of 7 Drawing Sheet(s) Filed in Color)
Specification includes a Sequence Listing.

(56) References Cited

OTHER PUBLICATIONS

Watts, J.K. et al., "Silencing Disease Genes in the Laboratory and the Clinic" Journal of Pathology (2012) vol. 226, pp. 365-379.
Li, J. et al., "Glycine Decarboxylase Mediates a Postbinding Step in Duck Hepatitis B Virus Infection" Journal of Virology (2004) vol. 78, No. 4, pp. 1873-1881.
Zhang, W.C. et al., "Glycine Decarboxylase Activity Drives Non-Small Cell Lung Cancer Tumor-Initiating Cells and Tumorigenesis" Cell (2012) vol. 148, pp. 259-272.
Li, X. et al., "Glycine Decarboxylase Expression Increased in p53-Mutated B Cell Lymphoma Mice" Oncology Research and Treatment (2015) vol. 38, No. 11, pp. 586-589.
Communication (Extended European Search Report) received in European Application No. 17865020.6 dated Jul. 31, 2020, 5 pages total.

* cited by examiner

ANTISENSE OLIGONUCLEOTIDES

CROSS-REFERENCE TO RELATED APPLICATIONS

This application is a U.S. National Phase application under 35 U.S.C. § 371 of International Patent Application No. PCT/SG2017/050517, filed on Oct. 16, 2017, which claims priority to Singapore Patent Application No. 10201609048R, filed on Oct. 28, 2016, all of which applications are incorporated herein by reference in their entireties.

SEQUENCE LISTING

The instant application contains a Sequence Listing which has been filed electronically in ASCII format and is hereby incorporated by reference in its entirety. Said ASCII copy, created on Sep. 23, 2019, is named 245866_000003_SL.txt and is 40,723 bytes in size.

The present invention relates to antisense oligonucleotides. In particular, the present invention relates to antisense oligonucleotides capable of inducing exon skipping of RNA.

More particular, the present application relates to the field of cancer, particularly to that of cancers overexpressing glycine decarboxylase (GLDC), such as non-small cell lung carcinoma (NSCLC) and other cancers such as lymphomas (e.g. follicular lymphoma, burkitt lymphoma, Diffuse Large B cell lymphoma), glioblastoma, breast-, prostate-, lung- and colon-cancer, etc. It is shown herein that direct and selective targeting of GLDC protein abundance (e.g. by antisense oligonucleotide (ASO)-mediated exon skipping), leads to cell cycle arrest and/or apoptosis of cancer cells. Also provided is evidence that partial depletion (e.g. by antisense oligonucleotide (ASO)-mediated exon skipping) of GLDC in normal tissue has no adverse effects.

GLDC is an enzyme belonging to the family of oxidoreductases, specifically those acting on the CH—$NH_2$ group of donors with a disulfide as acceptor. This enzyme participates in glycine, serine and threonine metabolism. It employs pyridoxal phosphate as a cofactor. GLDC is one of four proteins that form the glycine cleavage system in all eukaryotes which catalyzes the degradation of glycine. High levels of glycine in humans or glycine build up is known to glycine encephalopathy.

The listing or discussion of an apparently prior-published document in this specification should not necessarily be taken as an acknowledgement that the document is part of the state of the art or is common general knowledge.

Any document referred to herein is hereby incorporated by reference in its entirety.

In a first aspect of the present invention, there is provided an isolated antisense oligonucleotide for modulating the activity of GLDC.

Preferably, the term modulating refers to the activation, inhibition, delay, repression or interference of one or more of; the activity of GLDC; the RNA splicing or posttranslational processing to GLDC; the phosphorylation of GLDC; the level of expression of GLDC including both mRNA and/or pre-mRNA expression and protein expression; or the sub-cellular localisation of GLDC. Preferably, in the present invention, the oligonucleotide modulates one or more of activity; or level of pre-mRNA, matured mRNA and protein expression. In various embodiments, the oligonucleotide inhibits the expression of GLDC or modify its expression products. In particular embodiments, the oligonucleotide inhibits the expression of GLDC by inducing the skipping of an exon of a GLDC pre-mRNA or mature mRNA to induce cell cycle arrest and/or apoptosis. More particularly, the oligonucleotide inhibits the expression of GLDC in a cell that expresses GLDC.

Preferably, the oligonucleotide specifically hybridises to a target region of a GLDC pre-mRNA or mature mRNA. As used herein, "hybridisation" means an interaction between two or three strands of nucleic acids by hydrogen bonds in accordance with the rules of Watson-Crick DNA complementarity, Hoogstein binding, or other sequence specific binding known in the art. Hybridisation can be performed under different stringency conditions known in the art.

More preferably, the antisense oligonucleotide of the present invention exerts a steric hindrance effect against one or more RNA-binding splicing regulators. For example, in an embodiment, the oligonucleotide prevents translation of the mRNA by steric hindrance.

Preferably, the oligonucleotide specifically hybridises to an exon, intron or exon-intron boundary target region of a GLDC RNA, the target region is any one selected from the group comprising: exon 2, exon 3, exon 6, exon 7, exon 8, exon 9, exon 10, exon 12, exon 13, exon 15, exon 16, exon 19, exon 20, exon 21, intron 6, intron 7 and intron 8. These sequences are shown in the table below.

TABLE genomic sequences of target exons and introns

| Target | Sequence (5' to 3') | SEQ ID NO: |
|---|---|---|
| Exon 2 | agcattgatgaattgatcgagaagacggtccctgccaacatccgtttgaaaagacccttgaaaatggaagaccctgttt | 95 |
| Exon 3 | gtgaaaatgaaatccttgcaactctgcatgccatttcaagcaaaaaccagatctggagatcgtatattggcatgggctattataactgctca gtgccacagacgattttgcggaacttactggagaactcaggatg | 96 |
| Exon 6 | atatactggagtcctcactgagctgaagttaccctgtgaaatggacttcagtggaaaagatgtcagtggagtgttgttccagtacccagac acggaggggaaggtggaagacttttacggaactcgtggagagagctcatcagagtggg | 97 |
| Exon 7 | agcctggcctgctgtgctactgaccttttagctttgtgcatcttgaggccacctggagaatttggggtagacatcgccctgggcagctcccag agatttggagtgccactgggctatggggacccatgcagcattttttgctgtccgagaaagcttggtgagaatgatgcctggaagaatgg tgggggtaacaag | 98 |
| Exon 8 | agatgccactgggaaagaagtgtatcgtcttgctcttcaaaccagggagcaacacattcggagagacaaggctaccagcaacatctgtac agctcag | 99 |
| Exon 9 | gccctcttggcgaatatggctgccatgtttgcaatctaccatggttcccatgggctggagcatattgctaggagggtacataatgccactttg attttgtcagaag | 100 |
| Exon 10 | gtctcaagcgagcagggcatcaactccagcatgacctgttctttgataccttgaagattcagtgtggctgctcagtgaaggaggtcttggc agggccgctcagcggcagatcaattttcggcttttgaggatggcaca | 101 |

TABLE-continued genomic sequences of target exons and introns

| Target | Sequence (5' to 3') | SEQ ID NO: |
|---|---|---|
| Exon 12 | gaactggttgctgaaagcatgggagaggagtgcagaggtattccagggtctgtgttcaagaggaccagcccgttcctcacccatcaagtgttcaacag | 102 |
| Exon 13 | ctaccactctgaaacaaacattgtccggtacatgaagaaactggaaaataaagacatttcccttgttcacagcatgattccactg | 103 |
| Exon 15 | cctatcacatggaaagaatttgcaaacatccaccccttgtgcctctggatcaagctcaaggatatcagcagcttttccgagagcttgagaaggatttgtgtgaactcacaggttatgaccaggtctgtttccagccaaacag | 104 |
| Exon 16 | cggagcccaggagaatatgctggactggccactatccgagcctacttaaaccagaaaggagaggggcacagaacg | 105 |
| Exon 19 | gtgggaatctgtcgccctggagacttcgggtctgatgtctcgcacctaaatcttcacaagaccttctgcattcccacggaggaggtggtcctggcatggggcccatcggagt | 106 |
| Exon 20 | gaagaaacatctcgccccgttttttgcccaatcatcccgtcatttcactaaagcggaatgaggatgcctgtcctgtgggaaccgtcagtgcggcccccatggggctccagttccatcttgcccatttcctgggcttatatcaag | 107 |
| Exon 21 | atgatgggaggcaagggtcttaaacaagccacggaaactgcgatattaaatgccaactacatggccaagcgattagaaacacactacagaattcttttcaggggtgcaagag | 108 |
| Intron 6 | gtaggtatacctttcttgtgggggtccgtggaggcgtatcccaacttgtatctgtc-tacctatctctctctctgtctttttcatgtgccttaat<br>ttctttaccattatcacatggaatggtaaaactctccttcctgactccttgctgc-tactttttctgttcccggattcctggcacatggtgggc<br>actcagtatgtatttactgaatgaatgaatgagcaatggagttcacaggatgt-gaacacactctgcccgtcttcctgtagtaagataaattcc<br>tactctcccactactctcagggaaaggtagcaaccttgttccttttctctcacttcctttctag | 109 |
| Intron 7 | gtaaaggggctcatgttttctctacttttattgtgattatgatttccctgatttcttct-gatcacaaatgttgatttctatctgaattcaactggg<br>ccatgttgagtcagttaaggaaatgtacaacatagattcagaagaacaattctgtttgggatatgagctagtacttctcaaatactataaatttgtaaattttttgaaaaattttgtgtataattacaatgtatcgaagtcatgtaacgcat-ttgcttagattgatggacgccttgaaagactaaat<br>attttaggcatgttttgtgtctcgacagttttcgttctcaaaagcattatgccacgtggctctgtaaagacaaatgcactgagactgcaaagtacacactgagtttgctccgcgttcctcctagaggcttccgccacgtggccattt-gagtaatttccaaatgtactttcctgactgc<br>ttctcattggtgaaacttctcagattaaaaacgtagatgttcagaagtagtctttgttccttaaaaaaaaaagaaaagaaaagaaaaaaa<br>gggctgggtgcggtggctcacacctgtaatcccagcattctgggaggccgagtcaggcagatcacaaggtcaggagtcccagacgagcctggccaatatggtgaaaccctgtctttactaaaaatacaaaaattaggtgggcgtggtggtgggcgcctgtagtcccagctacttgggaggcagaggcaggagaatcacttgaaccacggaggtggaggttgcagtgagccgagatcgcgctgcctcactccagtttgggtgcagagcagactccatctcaaaaaaaaaaaagaaaaaaaaaggaaaaaaaaggagcggggaccctagatgcattccaggattattactgggaaatttagaaaaaaaaaattatgttttgacctttgataaaagctggactttaacataagtgagtaagctgaattagtcaatgatgtgatgataatgtgaagtgtgtttttttaaaattttatttatttattttattttattttgagaccaagtct-cactccatcacccaggctggagtgcagtggtgtaaa<br>cgtggccactgtgtccaactaattttttaaattttttgtaaaaacagggtttcaccatat-tgctcaggctggtcttagggctcaagtgatctgcc<br>cacccccagcctcccaaaatgctcggattaccaggtgtaagccaccatgcctggcctctgtatactttaaatcatcttattaacacctaatgttatgcaatggttgttacactgtattgttttttaaaaatttgtgtgatttgtttttttttttt-tattttttgagacggagtctctctctgtcacccag<br>gctggagtgcagtggtacgatcttggctcactgcaacctctgcctcccaggttcaagt-gattcttgagcctcagcctcccaagtaactgagatta<br>caggtgcctgtcaccatgtctggctaattttttgtatttttagtagagatggggtttcac-catgttggccaggctggtctcaaactctggacctc<br>aggtgatccgcccttggccccccaaagtgctgggattatagacatgagccgcgcggctcataaaatttgtgtgattttttaattgttgtattattttttattttttttgaatgttttcagtccgtgattggtg-gaatctgtggtgtagaatccacagagagccaagtcttttcaattttgtc<br>gtatatttccacttttcctgtgtctcctaagaagttcagagtgaaact-taatcctcccagtcaccattattgtatttgtctgggaaattcctgcaa<br>aattttctttcaaaattcctagacttattgtatatatcttggtgtctcagagta-cagtctaaaaatcagtaatcctgctgggcacagtggctca<br>tgcctgtaatcccagcactttgggaggccaaggcaggcggatcacctgaggccaggagttcaagaccagcctggccaacatggtgaaaccccatctctactaaaaatacaaaaattagctgggcgtggtgtcaggaggctgatgcagtagaatcgtttgaaaccagaaggcagaggttgcagtgagccgagatcacgccattgcactccagcctgggcgaaagagcgaaactccgtctcaaaaaaaaaaaaaaaatcagtaatcatgtttagatgaggaacgtttagaaattgtttctttataaatttgcacccaagtgcatttgctgaattcacttcaagctgggaaggaaagaagtaattctatttatagcatctcccagtgctgtgattatctgtgctaactgaatgccttattcttggtgtag | 110 |
| Intron 8 | gtaaatcacacgtctgacctgactactgaatgccttacgatacacagaaatgagctact-cattcattcattcatttgttcatttattcaccacc<br>tcctgagcagtgagcacaccagaaatggcaagatcttattggtgtagaaggctcattgtcttatgagaaccaaaatacagtattggctgggtacggtggctcatgcctgtaatcccacacccttgtgaggccaaggcagggtggattgctggaggttgaaacctgcctgggcgacatggcgaaacaccatctctatgaaaataaaataaaataaatttagccgtcagtggtggtatgctcctgtagtcccaggtgctagggaggctcaggtggaggatcaccagaatctgggaggttgaggctgcagtgagccatgattatgccactgcactccagcctgagtgacagagggagactctgtccccaactcctgcccccacaaaaaagtaaagaaaaagacactgtgttttactggtgttctttatatgtacaccatttgcctatgcttctcttcaccatacatgttttaatactaaaaaaaataaaaagcattatttgttt-cattttaccataatcacatcttcagatcctgaaca<br>ggcaaagcgtaagaaaggacaaaaaaggccagtcttcacttttatatacagacttaaaatatatgtaaatagaaagatggatatcaggtctctagtattcttggcgtttgggcaggtttgttatgggtggcagttgagacaccctctcttaggactgagaaggagcctctccaggaatgggttgaggaaggcaaagcaagggcatttgtgatgactgtgcttgagggatggtggtagtcatgaggcactcttactgggagattatgactggcattcttttttgttttttcgagacagagttttactctgtcgcccaggctg-gagtgcagtggcgcaatctcagctcactgcaacctctgctgcc<br>cggtttcaagcaattctcctgcctcagcctcctgagtaactgggattacaggcgcctgccacacgccaggctagttttttgcatttttagtagagacggggtttcaccatcttggccaggttggtcttgaactcctgacctcatgatccacccacctcggcctcccaaagtgttgggattacaagcatgagccactgcacctggccatgtctggcattcttttaaaggatgggataaaacaggaagagcttcctgggttctgaccaggggttctgggttctgctccttgaagtgctccagggcttaggtcgaagtgtttgtgaaacccagccaaaccctaggatcagttggaggcccactcctgagca | 111 |

TABLE-continued genomic sequences of target exons and introns

| Target | Sequence (5' to 3') | SEQ ID NO: |
|---|---|---|
| | caggatccattctaagtgcatctcttttttttttcttcttctttttttttcttcttt-gagatagagtcctgttcctgcgtcacccaggttggaatggggtggcgcaatcttggctcactgcaacctctgcctcctgggttcaagtgat-tcttgtgcctcagcctcctaaagagctggaattacaggcca | |
| | ccacacccagataattttttgtatttttagtagaggcaggtttcatcatgttggccaggctggtctcaaacgcctgacctcaagtgatggtcctgcctgggcctcccaaaattttgggattgtaggtgtgagc-catggcacctggcttctttttttttttttcttgagacagattcttgctctgttgtccattctggagtgcagtggcatggcatagctcactgcagcctcaaccttcaacctccaggctcaaattattctccggtctcagcctcctaagtagctgggactatgggtacattccaccacgcccagctaattttcaaaaaaatgttttgtagaggcgaggtctcactttgttgctcaggttggtctcaaattcctgagctcaagtgatcctatcttggcctcccatagtgataggattataggcatgagccaccgtgcctggccactgtaattgcatctcttccatgaagtgtcagagagagatgtcacaggtgcttcaatgggaggtagagtgctctttcgtctcagggctttggcgtctagaaccacctctgaaaagcttctccaggaaggcagtgggcaataagatcttcttatagttggttctgcagccacgggtctttggagccatttcctcagttggtccttttgtattatgttttgcctcaggaaggtgccacctcttttcaaatatgagctcttccagtatgataggaaggaaaggtggttggcacaggcttttcctctgttgaacagcaagctgatctttatttatttat-ttgttttttttggttgttttttttttttttgagatggagtcttgctctgtc | |
| | acccaggctggcatgcagcggcccaatctcagct-cactgcaacctctgccttccagttttccagcgattctcttgcctcagcctcctgagtagctgggattacaggcgcctgccaccatgcccaactaatttttctatttttagtaga-gacagggtttcaccatgttggtcaggctggtctcgaactcctg | |
| | atctcatgatctgcccacctcggcctcccaaagtgctgggattacaggcataagccgccatgcctggccacatggtgatctttatatggtggcctcacttttctgtagcttacccctccatttgttgaattctctgct-tactgttttcccttcggtgcagctgactgctcctgtcttgctgtttctcct | |
| | caggttcctccaggtttccgtctgatcataagtccatt-tagggcctcagttttctgcctctaggttcattttccaggtgaatttgggctgtctgcagtgaaccagttatgttcctgtttctttcttttttttttttttgagacg-gagtctttctcttgttgcccaggctggagtgcaatggcgtgatgtcggctcactgcaacctccgtctccggggttcaagcgatactcctgcctcagcctcct-gagtagctgggattacaggcacccacgaccatgcctggctaatattttttgtatttttagtagagatggggtttcac-catgctggccaggctggtctcgaactcctgacctcaggtgatccgcccgccttggcctcccaaagtgctgggattacaggcatgagccattgtgcccggcctatgttcctgttgct-taatttcttccagttcatgtatagctgataaatttat | |
| | tatttaacttgggttgaaaggtctgtatcttttccagcaattgttaaaatgtttgccctg-gagatggccatactccagcttgtctgattttcatcctcttattctgatgatcttctaactcttcactgtctatttcactgcatatgtgccttttt-catagttgattgcatacaagaattactcataactcca | |
| | gtttcactctttgtgagcatgcaagtctccctgttttgttag-gagatgactggtgtcttttgagttgttccttttgtgctgtaggtctttgaccccgcctcctgttgtagcagctgttccacattcttctcactcttgctcttctctcttgt-cactgggtgggtggggagtccactcttagtttcgcatcgtggatggggcatgactcttttttaatctctgaaagtgtgttaatgattcttttt-taaataaattttctatagggagtctctctgagcctatt | |
| | ctggctcagcaggccccattctaaaacaaaactgaaaaaacagggtgcggtggctcacacctgtaatctcaacactttaggaggccaaggcaggaggattacttgagttcagcagtttaaatccatcccaggcaacatagtgaagctcctgtctatataaaaaaagtacaaaaattagccaggtgttgtggtacacaccagtatcccagctactcagtagactgaggtggtaggagtgcttgagctgggaggtccaggctgcagtgagctgcaatcacaccactgcactccaacctgggtgacagaatcagaccccacctctacaaaacaaaaaggaaaagaaacaattttttctataaatttgtggcattactacagatgtctgaattttcattatgttctgttctttatattctcttat-ttctttttttttttggagacgagtctcgctccatcgcccaggctggagtgcagtagcgccatctcgctcactgaagctctgcctcccgggttcacgc-cattctcctgcctcagcctcctgtgtagctggga | |
| | ctacaggtgtctgctaccatgcctggctaatttattgtatttttagtagatacagggttt-caccatgttagcaggatggtctcgatctcctgacctcatgatccacctgcctcagcctcccaaagtgctgggattacaggcgttagccac-catgcccggccatatattctcttatttcttagcttctaccacaatgagcagctctttcattggcttttcttattttttaatataaaaatctttt-taaaatagagatgggagtcttactttgttgcccaggcta | |
| | gtattgatctccaggcctcaagcgatcctcctgcctcagcctcccaaagtgttgggatcactggtgtgagccactgcatccagccttgttggcttttctaaagtcaggtgtagtaaagaataattttacacttttattagctttttttatt-gagatgtaactcaccgtaagtttcaccaattgcaagtat | |
| | acagctcaatggttttactctatttacaaggttgtgcaactatcaccagtatttaat-ttcagaatattttttattacccccaaaaagaaattctattcctatgaagtagtcactcctcatccctctccccttcctatagcccctggcaactactat-tctactttctgtctccctggatttgcctgttctgaa | |
| | tatttcatataaatgggatcatacaatgtgtggccttttgtacctggcttcttttgcat-aaggttttcaaggttcatccatattgtagcatgaatgtgtacttaattcttttctatggctgggtaatatcccattgtttggacatgctacat-tttgtttatccattcatcaattggtaaacatttgggggtgt | |
| | ttcaaataagcctgctgtgaacacttctgtgtaaattttttgtatg-gatgtaatgttttcagttcttttggttatattcctagcagtgaaattgctgggtcatataactctacatttaacattttgaggaacttccagacatttttcaaagtggctg-cattattttactttcctaccagcagcatatgaat | |
| | attctaatttctccgtattttcaccaatgcttgttacttcctatccttttggttatagc-catcctattggatgtcaagtgataatctcactgtggttttgttttgtatttccctaataactaatgattttgagcattcattagcttttgaggcttt-taagtacctaattgtattattgttattttatttatt | |
| | tattttagagatggggtcttgttatgttcttcttgctggtctt-taactcctgggctaaagcaatcctcccacccttagcctcccaaagtcttgggattacaggcgtgagccactgattcaagccctttgtatttttaagtttgttcaattttgt-gaaagaaattgtcattttcttggtctctattttaatttttt | |

TABLE-continued genomic sequences of target exons and introns

| Target | Sequence (5' to 3') | SEQ ID NO: |
|---|---|---|
| | ttggttcttcttttgatattctagtgcccttttgaagtttttaaaaagtggttt-tatacttctcatcaatttgttgttcagccgtgtgatatagcct cctgattatggaaggaatcatctgtagattaaaaagggacatgaaccaacctctacaat-attgtggtggaggctgccagggcattctgtgaatgtc aggcctgggttctgtttccagcaacacagccatgagcatttgggcacagtgtgtcacagattctttacctcagcctcgccttttccacagct gtaaagtgctgtggagtttctgtgtttatttctgattgttgtaaggagtccat-aagagtgtttacactttgtctaggacttttagtacaagaatg cctacttccatgttttctgatgtctctttctcctcatttacttccttgtttgctgactt-cacctttggaaactgtttcttattttgcattggctcc atagagacttcctctagtagtctagcagaaaaaaagatgtacctaacaaaatggacccagtattgaacatcaactgtattttgcagagacagg gttttgtattgtcaaccgggctggagtccagtggcgcaatcataggtcactgtaacctcgaaatcctgggttcaagtgatccatctcggcttc tggagtcactgggactacagttgcacaccaccccgctcccagctgaagtgcgcattgccgttttttgccagtcctttgccacagattctccatt caactcttggttggcagaagttcagcctctagtgtttttatttaagttcttaggagaatt-tattcctgaagttcttgaatgtttgaaaattgctt gtttcttttattcttgaagaattgcctggttgagtgtaaaattctcagatct-cacttttttctccctgaggtctttattgcttcactgtcttccaa cattaaacattgcttctcaatgtctgatggtagtgtgatctttgcccttaagggtgacat-gattttgttgcatggaagaagcccttcgtaatggt caaatgtgaaggtttagtatagtaacaactccagggtgtcttggatgatggttcctttcaggtagtcaggcaggttatatattaattgtcccc aactatcaaagaatgtaggaaatctgatcattttgttttgtcgctgtcttcagttttga-catcccaagtcaagtaattacaccctcccactaat tgtcctccatcacgtgattcttttaaatgttcttatcttttag | |

Preferably, the antisense oligonucleotide comprises a sequence selected from any one of SEQ ID NOs: 1 to 94. SEQ ID Nos: 1 to 12 are shown in Table 1. In addition to those sequences shown in Table 1, Table 2 shows alternative sequences of shAONs (SEQ ID Nos: 13 to 94) that are also capable of inducing exon skipping in GLDC transcripts.

TABLE 1

| SEQ ID NO. | shAON Label | shAON formula (5'-3') |
|---|---|---|
| 1 | 8a | UUG UCU CUC CGA AUG UGU UGC UCC CUG GUU |
| 2 | 8b | UGU UGC UCC CUG GUU UGA AGA GCA AGA CG |
| 3 | 8c | GGU AGC CUU GUC UCU CCG AAU GUG UUG C |
| 4 | 8d | UCU CUC CGA AUG UGU UGC UCC CUG GUU UGA |
| 5 | 13a | UGU GAA CAA GGG AAA UGU CUU UAU UUU C |

TABLE 1-continued

| SEQ ID NO. | shAON Label | shAON formula (5'-3') |
|---|---|---|
| 6 | 13c | GUU UCU UCA UGU ACC GGA CAA UGU UUG UUU |
| 7 | 13d | AUG UCU UUA UUU UCC AGU UUC UUC AUG UA |
| 8 | 16b | UUU CUG GUU UAA GUA GGC UCG GAU AGU G |
| 9 | 7a | AGG UGG CCU CAA GAU GCA CAA AGC UAA AAG G |
| 10 | 7b | AUU CUC CAG GUG GCC UCA AGA UGC ACA AAG |
| 11 | 7c | AAG CUA AAA GGU CAG UAG CAC AGC AGG CCA GG |
| 12 | 7d | AAG GUC AGU AGC ACA GCA GGC CAG GCU |

TABLE 2

| SEQ ID NO. | |
|---|---|
| 13 | 5'-GUU GGC AGG GAC CGU CUU CUC GAU CAA UUC AUC AAU-3' |
| 14 | 5'-UUC AAA CGG AUG UUG GCA GGG ACC GUC UUC-3' |
| 15 | 5'-GGC AUG CAG AGU UGC AAG GAU UUC AUU UUC A-3' |
| 16 | 5'-UUU UUG CUU GAA AUG GCA UGC AGA GUU GCA AGG AUU-3' |
| 17 | 5'-UCU GGU UUU UGC UUG AAA UGG CAU GCA GAG UU-3' |
| 18 | 5'-AUA UAC GAU CUC CAG AUC UGG UUU UUG CUU GA-3' |
| 19 | 5'-AGU UAU AAU AGC CCA UGC CAA UAU-3' |
| 20 | 5'-CUG UGG CAC UGA GCA GUU AUA AUA-3' |
| 21 | 5'-UCC ACU GAC AUC UUU UCC ACU GAA GUC CAU UUC ACA GGG-3' |
| 22 | 5'-GGG UAC UGG AAC AAC ACU CCA CUG ACA UCU UUU C-3' |

TABLE 2-continued

| SEQ ID NO. | |
|---|---|
| 23 | 5'-CUC CGU GUC UGG GUA CUG GAA CAA CAC UCC ACU-3' |
| 24 | 5'-AGU UCC GUA AAG UCU UCC ACC UUC CCC UCC GUG UCU GGG-3' |
| 25 | 5'-UGA UGA GCU CUC UCC ACG AGU UCC GUA AAG-3' |
| 26 | 5'-AAA GCU AAA AGG UCA GUA GCA CAG CAG GCC AGG CU-3' |
| 27 | 5'-CAA GAU GCA CAA AGC UAA AAG GUC AGU AGC ACA GCA-3' |
| 28 | 5'-AGG UGG CCU CAA GAU GCA CAA AGC UAA AAG GUC-3' |
| 29 | 5'-AAU UCU CCA GGU GGC CUC AAG AUG CAC AAA GCU AA- 3' |
| 30 | 5'-UCU ACC CCA AAU UCU CCA GGU GGC CUC AAG A- 3' |
| 31 | 5'-AAA UCU CUG GGA GCU GCC CAG GGC GAU GUC U-3' |
| 32 | 5'-CCC CCA UAG CCC AGU GGC ACU CCA AAU CUC UG-3' |
| 33 | 5'-AAA AAU GCU GCA UGG GGU CCC CCA UAG CCC AGU-3' |
| 34 | 5'-CGG ACA GCA AAA AUG CUG CAU GGG GUC CCC C-3' |
| 35 | 5'-AGA CGA UAC ACU UCU UUC CCA GUG GCA UCU-3' |
| 36 | 5'-CUG GUU UGA AGA GCA AGA CGA UAC ACU UCU UUC-3' |
| 37 | 5'-GAA UGU GUU GCU CCC UGG UUU GAA GAG CAA GAC GA-3' |
| 38 | 5'-CUU GUC UCU CCG AAU GUG UUG CUC CCU GGU UUG A-3' |
| 39 | 5'-UGG UAG CCU UGU CUC UCC GAA UGU GUU GCU CCC U-3' |
| 40 | 5'-GAU GUU GCU GGU AGC CUU GUC UCU CCG AAU GUG UUG-3' |
| 41 | 5'-GUA CAG AUG UUG CUG GUA GCC UUG UCU CUC CGA AUG-3' |
| 42 | 5'-GAA CCA UGG UAG AUU GCA AAC AUG GCA GC-3' |
| 43 | 5'-CAA AAU CAA AGU GGC AUU AUG UAC CCU CCU AGC AA-3' |
| 44 | 5'-AUG CUG GAG UUG AUG CCC UGC UCG CUU GAG A-3' |
| 45 | 5'-CAA GGU AUC AAA GAA CAG GUC AUG CUG GAG UUG AU-3' |
| 46 | 5'-AAU CUU CAA GGU AUC AAA GAA CAG GUC AUG CUG G-3' |
| 47 | 5'-CCU CCU UCA CUG AGC AGC CAC ACU GAA UCU UCA AGG UA-3' |
| 48 | 5'-GAU CUG CCG CUG AGC GGC CUG CCA AGA CUC CUU CA-3' |
| 49 | 5'-UCU UGA ACA CAG ACC CUG GAA UAC CUC UGC A-3' |
| 50 | 5'-UGA UGG GUG AGG AAC GGG CUG GUC CUC UU-3' |
| 51 | 5'-UCA UGU ACC GGA CAA UGU UUG UUU CAG AGU GGU AG-3' |
| 52 | 5'-AGU UUC UUC AUG UAC CGG ACA AUG UUU GUU UC-3' |
| 53 | 5'-UAU UUU CCA GUU UCU UCA UGU ACC GGA CAA UGU UUG-3' |
| 54 | 5'-AAG GGA AAU GUC UUU AUU UUC CAG UUU CUU CAU GUA-3' |
| 55 | 5'-GAA CAA GGG AAA UGU CUU UAU UUU CCA GUU UCU UCA-3' |
| 56 | 5'-UGU GAA CAA GGG AAA UGU CUU UAU UUU CCA GUU U-3' |
| 57 | 5'-CAG UGG AAU CAU GCU GUG AAC AAG GGA AAU GUC UUU A-3' |
| 58 | 5'-GGG GUG GAU GUU UGC AAA UUC UUU CCA GUG AUA GG-3' |
| 59 | 5'-AAA GGG GUG GAU GUU UGC AAA UUC UUU CCA UG-3' |
| 60 | 5'-UCC AGA GGC ACA AAG GGG UGG AUG UUU GCA AA-3' |

TABLE 2-continued

| SEQ ID NO. | |
|---|---|
| 61 | 5'-GCU GAU AUC CUU GAG CUU GAU CCA GAG GCA CAA AGG-3' |
| 62 | 5'-AAA GCU GCU GAU AUC CUU GAG CUU GAU CCA GAG GCA C-3' |
| 63 | 5'-AAA UCC UUC UCA AGC UCU CGG AAA AGC UGC UGA UA- 3' |
| 64 | 5'-UUC ACA CAA AUC CUU CUC AAG CUC UCG GAA AAG-3' |
| 65 | 5'-UCA UAA CCU GUG AGU UCA CAC AAA UCC UUC-3' |
| 66 | 5'-GAU AGU GGC CAG UCC AGC AUA UUC UCC CUG GGC UCC G-3' |
| 67 | 5'-AGU AGG CUC GGA UAG UGG CCA GUC CAG CAU AUU CUC-3' |
| 68 | 5'-GUU UAA GUA GGC UCG GAU AGU GGC CAG UCC AGC AUA-3' |
| 69 | 5'-CUG GUU UAA GUA GGC UCG GAU AGU GGC CAG UCC A-3' |
| 70 | 5'-UCU CCU UUC UGG UUU AAG UAG GCU CGG AUA GUG-3' |
| 71 | 5'-GUU CUG UGC CCC UCU CCU UUC UGG UUU AAG UAG GCU-3' |
| 72 | 5'-CGA GAC AUC AGA CCC GAA GUC UCC AGG GCG ACA GAU U-3' |
| 73 | 5'-AGA UUU AGG UGC GAG ACA UCA GAC CCG AAG UC-3' |
| 74 | 5'-GAA GGU CUU GUG AAG AUU UAG GUG CGA GAC AUC AGA-3' |
| 75 | 5'-AUG CAG AAG GUC UUG UGA AGA UUU AGG UGC GAG-3' |
| 76 | 5'-CGU GGG GAA UGC AGA AGG UCU UGU GAA GAU UUA-3' |
| 77 | 5'-CUC CUC CGU GGG GAA UGC AGA AGG UCU UGU G-3' |
| 78 | 5'-CAU GCC AGG ACC ACC UCC UCC GUG GGG AAU GCA GAA G-3' |
| 79 | 5'-UGG GCC CCA UGC CAG GAC CAC CUC CUC CGU GGG-3' |
| 80 | 5'-GAU GAU UGG GCA AAA ACG GGG CGA GAU GUU U-3' |
| 81 | 5'-GCU UUA GUG AAA UGA CGG GAU GAU UGG GCA AAA-3' |
| 82 | 5'-AUU CCG CUU UAG UGA AAU GAC GGG AUG AUU-3' |
| 83 | 5'-AGG CAU CCU CAU UCC GCU UUA GUG AAA UG-3' |
| 84 | 5'-ACU GGA GCC CCA UGG GGC CGC ACU G-3' |
| 85 | 5'-CCG UGG CUU GUU UAA GAC CCU UGC CUC CCA UCA U-3' |
| 86 | 5'-AUC GCA GUU UCC GUG GCU UGU UUA AGA CCC UUG CC-3' |
| 87 | 5'-CAU UUA AUA UCG CAG UUU CCG UGG CUU GUU UAA G-3' |
| 88 | 5'-UGU AGU UGG CAU UUA AUA UCG CAG UUU CCG U-3' |
| 89 | 5'-UCG CUU GGC CAU GUA GUU GGC AUU UAA UAU CGC AGU-3' |
| 90 | 5'-UUC UAA UCG CUU GGC CAU GUA GUU GGC AUU UAA UAU-3' |
| 91 | 5'-UGU UUC UAA UCG CUU GGC CAU GUA GUU GGC AUU U-3' |
| 92 | 5'-UCU GUA GUG UGU UUC UAA UCG CUU GGC CAU GUA GUU-3' |
| 93 | 5'-AAA AGA AUU CUG UAG UGU GUU UCU AAU CGC UUG-3' |
| 94 | 5'-CCU GAA AAG AAU UCU GUA GUG UGU UUC UAA UC-3' |

In various embodiments of the present invention, each sequence set out in Table 1 or Table 2 may target one or more exon/intron.

By "oligonucleotide", it is meant to refer to any polynucleotide. A "polynucleotide" is an oligomer comprised of nucleotides. A polynucleotide may be comprised of DNA, RNA modified forms thereof, or a combination thereof. The term "nucleotide" or its plural as used herein is interchangeable with modified forms as discussed herein and otherwise known in the art. In certain instances, the art uses the term "nucleobase" which embraces naturally occurring nucleotides as well as modifications of nucleotides that can be polymerized. Thus, nucleotide or nucleobase means the naturally occurring nucleobases adenine (A), guanine (G), cytosine (C), thymine (T) and uracil (U) as well as non-naturally occurring nucleobases such as xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C[3]-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et ah, U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et ah), in Chapter 15 by Sanghvi, in Antisense Research and Application, Ed. S. T. Crooke and B. Lebleu, CRC Press, 1993, in Englisch et ah, 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which is hereby incorporated by reference in its entirety). In various aspects, polynucleotides also include one or more "nucleosidic bases" or "base units" which include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles {e.g., 5-nitroindole), and optionally substituted hypoxanthine. Other desirable universal bases include pyrrole, and diazole or triazole derivatives, including those universal bases known in the art.

Polynucleotides may also include modified nucleobases. A "modified base" is understood in the art to be one that can pair with a natural base {e.g., adenine, guanine, cytosine, uracil, and/or thymine) and/or can pair with a non-naturally occurring base. Exemplary modified bases are described in EP 1 072 679 and WO 97/12896, the disclosures of which are incorporated herein by reference. Modified nucleobases include, without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (IH-pyrimido[5,4-b] [1,4]benzoxazin-2(3H)-one), phenothiazine cytidine (IH-pyrimido[5,4-b] [1,4]benzothiazin-2(3H)-one), G-clamps such as a substituted phenoxazine cytidine (e.g. 9-(2-aminoethoxy)-H-pyrimido[5,4-b] [1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deazaadenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et ah, 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity of the polynucleotide and include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.deg. C. and are, in certain aspects, combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Those of skill in the art can readily design antisense polynucleotides according to the present disclosure. For example, general teachings in the art include, but are not limited to, Wee and Pramono et al, PLoS One 3:e1844 (2008); Pramono Z A et al, WO/2011/078,797; Pramono and Wee et al, Hum Gene Ther 23:781-790 (2012); Aartsma-Rus et al, Methods Mol Biol. 867: 117-29 (2012); Aartsma-Rus et al, Methods Mol Biol. 867: 97-116 (2012); van Roon-Mom et al., Methods Mol Biol. 867: 79-96 (2012), each of which is incorporated herein by reference. General guidelines also include attempting to avoid 3 consecutive G or C nucleotides, choosing lengths and sequences that do not favour formation of self-structures (hairpinning will be avoided), and avoiding those sequences likely to form primer dimers. In some embodiments, an antisense polynucleotide of the disclosure is one that is designed to specifically hybridize to an exon or an intron or an intron-exon boundary, such that the antisense polynucleotide specifically hybridises to a sequence that is completely within an exon of a PRDM15 nucleic acid, or about one nucleotide of the antisense polynucleotide spans said intron-exon boundary when the antisense polynucleotide is specifically hybridised to the PRDM15 nucleic acid. In some embodiments wherein the antisense polynucleotide specifically hybridizes to a sequence that is completely within an exon, it is contemplated that a terminus of the antisense polynucleotide is about 1, 2, 3, 4, 5, 6, 7, 8, 9, 10 or more nucleotides from a terminus of the exon.

In other embodiments, an antisense polynucleotide of the disclosure is one that is designed to specifically hybridize to an intron-exon boundary of a GLDC nucleic acid, such that about 2, 3, 4, 5, 6, 7, 8, 9, 10 or more nucleotides of the antisense polynucleotide span said intron-exon boundary. It is understood that a nucleotide can "span the intron-exon boundary" on either the exon side or intron side. Thus, an antisense polynucleotide that specifically and predominantly hybridises to intronic sequence and only hybridizes to one nucleotide of an adjoining exon would "span the intron-exon boundary" by one nucleotide. Similarly, an antisense polynucleotide that specifically hybridizes to exonic sequence and only hybridises to one nucleotide of an adjoining intron would "span the intron-exon boundary" by one nucleotide. In any of the aforementioned embodiments, the antisense polynucleotide is at least about 10 nucleotides and up to about 15, 20, 25, 30, 35, 40, 45, 50 or more nucleotides in length.

Preferably, the antisense oligonucleotide may comprise a modified polynucleotide backbone. The modified polynucleotide backbone may comprise a modified moiety substituted for the sugar of at least one of the polynucleotides.

Modified polynucleotides are contemplated for use wherein both one or more sugar and/or one or more internucleotide linkage of the nucleotide units in the polynucleotide is replaced with "non-naturally occurring" sugars (i.e., sugars other than ribose or deoxyribose) or internucleotide linkages, respectively. In one aspect, this embodiment contemplates a peptide nucleic acid (PNA). In PNA compounds, the sugar-backbone of a polynucleotide is replaced with an amide-containing (e.g., peptide bonds between N-(2-aminoethyl)-glycine units) backbone. See, for example U.S. Pat. Nos. 5,539,082; 5,714,331; and 5,719,262, and Nielsen et ah, Science, 1991, 254, 1497-1500, the disclosures of which are herein incorporated by reference. Modified polynucleotides may also contain one or more substituted sugar groups. In one aspect, a modification of the sugar includes Locked Nucleic Acids (LNAs) in which the 2'-hydroxyl group is linked to the 3' or 4' carbon atom of the sugar ring, thereby forming a bicyclic sugar group. The linkage is in certain aspects a methylene ($-CH_{[2]}-)_{[n]}$ group bridging the 2' oxygen atom and the 4' carbon atom wherein n is 1 or 2. LNAs and preparation thereof are described in WO 98/39352 and WO 99/14226, the disclosures of which are incorporated herein by reference. In the present invention, preferably, the antisense oligonucleotide comprises a modified polynucleotide backbone. The modified polynucleotide backbone may comprise a modified moiety substituted for the sugar of at least one of the polynucleotides. The modified moiety may be selected from the group comprising of phosphorodiamidate morpholino oligomer (PMO), peptide-conjugated phosphorodiamidate morpholino oligomer (PPMO), and non-peptide dendrimeric octaguanidine moiety-tagged morpholino oligomer.

In various embodiments, the modified polynucleotide backbone comprises at least one modified internucleotide linkage. The modified internucleotide linkage comprises a modified phosphate. More preferably, the modified phosphate is any one selected from the group comprising of a non-bridging oxygen atom substituting a sulfur atom, a phosphonate, a phosphorothioate, a phosphodiester, a phosphoromorpholidate, a phosphoropiperazidate and a phosphoroamidate.

In various embodiment of the invention, the antisense oligonucleotide comprises a backbone selected from the group comprising of ribonucleic acid, deoxyribonucleic acid, DNA phosphorothioate, RNA phosphorothioate, 2'-O-methyl-oligoribonucleotide and 2'-O-methyl-oligodeoxyribonucleotide, 2'-O-hydrocarbyl ribonucleic acid, 2'-O-hydrocarbyl DNA, 2'-O-hydrocarbyl RNA phosphorothioate, 2'-O-hydrocarbyl DNA phosphorothioate, 2'-F-phosphorothioate, 2'-F-phosphodiester, 2'-methoxyethyl phosphorothioate, 2-methoxyethyl phosphodiester, deoxy methylene(methylimino) (deoxy MMI), 2'-O-hydrocarby MMI, deoxymethylphos-phonate, 2'-O-hydrocarbyl methylphosphonate, morpholino, 4'-thio DNA, 4'-thio RNA, peptide nucleic acid, 3'-amidate, deoxy 3'-amidate, 2'-O-hydrocarbyl 3'-amidate, locked nucleic acid, cyclohexane nucleic acid, tricycle-DNA, 2'fluoro-arabino nucleic acid, N3'-P5' phosphoroamidate, carbamate linked, phosphotriester linked, a nylon backbone modification and mixtures of the aforementioned backbones.

Preferably, the oligonucleotide is chemically linked to one or more conjugates that enhance the activity, cellular distribution, or cellular uptake of the antisense oligonucleotide.

The compounds of the disclosure also can be used as a prophylactic or therapeutic, which may be utilized for the purpose of treatment of a genetic disease. In an embodiment, the antisense oligonucleotide may be used in treating a GLDC-expressing cancer patient. The patient may be administered a further anti-cancer agent or treatment. The cancer is any one selected from the group comprising: non-small cell lung carcinoma (NSCLC), breast cancer, ovarian cancer, haematological malignancies, lung cancer, prostate cancer, stomach cancer, testis cancer, larynx cancer, liver cancer, uterus cancer, colorectal cancer, melanoma, glioblastoma, sarcomas, retinoblastoma, thyroid cancer, and glioma, carcinoid and phyllode tumours. The haematological malignancies is either lymphoma or leukaemia. In particular, the lymphoma is a B-cell lymphoma. More particularly, the B-cell lymphoma is a follicular lymphoma or a diffuse large B-cell lymphoma.

In another aspect of the present invention, there is provided a pharmaceutical composition comprising the antisense oligonucleotide according to the first aspect of the invention and a pharmaceutically acceptable carrier. The composition is suitable for parenteral administration either naked or complexed with a delivery agent to a patient. The carrier is selected from the group consisting of a nanoparticle, such as a polymeric nanoparticle; a liposome, such as pH-sensitive liposome, an antibody conjugated liposome; a viral vector, a cationic lipid, a polymer, a UsnRNA, such as U7 snRNA and a cell penetrating peptide. The antisense oligonucleotide is administered orally, or rectal, or transmucosal, or intestinal, or intramuscular, or subcutaneous, or intramedullary, or intrathecal, or direct intraventricular, or intravenous, or intravitreal, or intraperitoneal, or intranasal, or intraocular.

A pharmaceutically acceptable carrier refers, generally, to materials that are suitable for administration to a subject wherein the carrier is not biologically harmful, or otherwise, causes undesirable effects. Such carriers are typically inert ingredients of a medicament. Typically a carrier is administered to a subject along with an active ingredient without causing any undesirable biological effects or interacting in a deleterious manner with any of the other components of a pharmaceutical composition in which it is contained. Suitable pharmaceutical carriers are described in Martin, Remington's Pharmaceutical Sciences, 18th Ed., Mack Publishing Co., Easton, Pa., (1990), incorporated by reference herein in its entirety.

In a more specific form of the disclosure there are provided pharmaceutical compositions comprising therapeutically effective amounts of an antisense polynucleotide together with pharmaceutically acceptable diluents, preservatives, solubilizers, emulsifiers, adjuvants and/or carriers. Such compositions include diluents of various buffer content (e.g., phosphate, Tris-HCl, acetate), pH and ionic strength and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as, for example and without limitation, polylactic acid or polyglycolic acid, or into liposomes. Hylauronic acid may also be used. Such compositions may influence the physical state, stability, rate of in vivo release, and rate of in vivo clearance of the disclosed compositions. The compositions may be prepared in liquid form, or may be in dried powder, such as lyophilized form.

It will be appreciated that pharmaceutical compositions provided according to the disclosure may be administered by any means known in the art. Preferably, the pharmaceutical compositions for administration are administered by injection, orally, or by the pulmonary, or nasal route. The antisense polynucleotides are, in various embodiments, delivered by intravenous, intra-arterial, intraperitoneal, intramuscular, or subcutaneous routes of administration.

The antisense molecules of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

For polynucleotides, preferred examples of pharmaceutically acceptable salts include, but are not limited to, (a) salts formed with cations such as sodium, potassium, ammonium, magnesium, calcium, polyamines such as spermine and spermidine; (b) acid addition salts formed with inorganic acids, for example hydrochloric acid, hydrobromic acid, sulfuric acid, phosphoric acid, nitric acid; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid; and (d) salts formed from elemental anions such as chlorine, bromine, and iodine. The pharmaceutical compositions of the disclosure may be administered in a number of ways depending upon whether local or systemic treatment is desired and upon the area to be treated. Administration may be topical (including ophthalmic and to mucous membranes including rectal delivery), pulmonary, e.g., by inhalation of powders or aerosols, (including by nebulizer, intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration. Polynucleotides with at least one 2'-0-methoxyethyl modification are believed to be particularly useful for oral administration.

The pharmaceutical formulations of the disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly bringing into association the active ingredients with liquid carriers or finely divided solid carriers or both, and then, if necessary, shaping the product.

Combination therapy with an additional therapeutic agent is also contemplated by the disclosure. Examples of therapeutic agents that may be delivered concomitantly with a composition of the disclosure include, without limitation, a glucocorticoid steroid (for example and without limitation, prednisone and deflazacort), an angiotensin converting enzyme inhibitor, a beta adrenergic receptor blocker, an anti-fibrotic agent and a combination thereof.

In some embodiments, the present invention may be used in gene therapy such, e.g. using a vector (e.g., an expression vector) comprising a polynucleotide of the invention to direct expression of the polynucleotide in a suitable host cell. Such vectors are useful, e.g., for amplifying the polynucleotides in host cells to create useful quantities thereof, and for expressing proteins using recombinant techniques. In some embodiments, the vector is an expression vector wherein a polynucleotide of the invention is operatively linked to a polynucleotide comprising an expression control sequence.

As such, yet another aspect of the present invention provides for a method of treating cancer in a patient, the method comprising administering an antisense oligonucleotide according to the first aspect of the invention, or a pharmaceutically effective amount of a composition comprising the antisense oligonucleotide. The carrier is selected from the group consisting of a nanoparticle, such as a polymeric nanoparticle; a liposome, such as pH-sensitive liposome, an antibody conjugated liposome; a viral vector, a cationic lipid, a polymer, a UsnRNA, such as U7 snRNA and a cell penetrating peptide.

The antisense oligonucleotide or composition may be administered orally, or rectal, or transmucosal, or intestinal, or intramuscular, or subcutaneous, or intramedullary, or intrathecal, or direct intraventricular, or intravenous, or intravitreal, or intraperitoneal, or intranasal, or intraocular. Having said that, proven systemic administration options include intravenous, intraperitoneal, intranasal and intrathecal. Complexing of ASOs with delivery carriers such as nanoparticles, polymer- or liposome-based vehicles can further augment the delivery efficiency of ASOs to specific tissues.

The cancer may be any one selected from the group comprising: haematological malignancies, lung cancer, breast cancer, prostate cancer, stomach cancer, testis cancer, larynx cancer, liver cancer, uterus cancer, colorectal cancer, melanoma, glioblastoma, sarcomas, and retinoblastoma.

In an embodiment, the cancer is non-small cell lung carcinoma (NSCLC).

In yet another aspect of the present invention, there is provided the use of an antisense oligonucleotide that modulates the activity of GLDC in the manufacture of a medicament for treating cancer. The oligonucleotide modulates one or more of activity; or level of pre-mRNA, matured mRNA and protein expression. In an embodiment, the cancer is non-small cell lung carcinoma (NSCLC).

In another aspect of the present invention, there is provided a method for aiding in categorising or determining prognosis in a patient with cancer, or in selecting a therapeutic strategy for a patient with cancer, the method comprising assessing the level of GLDC nucleic acid, protein or activity in a sample. The method comprises the step of selecting a treatment regime making use of the information on the level of GLDC nucleic acid, protein or activity in the sample. In various embodiments, the sample is obtained from the patient and the sample is a tissue sample in which cancer is suspected or in which cancer has been found, or contains cells from said tissue. If the level of GLDC nucleic acid, protein or activity in the sample is an elevated level, then the selected treatment regime comprises treating the patient with an inhibitor of GLDC activity or modulator of GLDC's pre-mRNA, mRNA and protein expression levels.

In various embodiments, the inhibitor or modulator comprises an antisense oligonucleotide according to the first aspect of the present invention.

In another aspect of the present invention, there is provided a method of inducing exon-skipping of a GLDC pre-mRNA, the method comprising delivering to a cell the antisense polynucleotide according to the first aspect of the present invention, or the pharmaceutical composition comprising the antisense oligonucleotide, thereby inducing exon-skipping of the GLDC pre-mRNA.

Preferably, any one of exon 2, exon 3, exon 6, exon 7, exon 8, exon 9, exon 10, exon 12, exon 13, exon 15, exon 16, exon 19, exon 20, or exon 21 is skipped.

In various embodiments, the cell may be a human cell. The human cell is a cancer cell, the cancer is any one selected from the group comprising: NSCLC, haematological malignancies, lung cancer, breast cancer, prostate cancer, stomach cancer, testis cancer, larynx cancer, liver cancer, uterus cancer, colorectal cancer, melanoma, glioblastoma, sarcomas, and retinoblastoma.

In another aspect of the present invention, there is provided a kit comprising the antisense oligonucleotide according to the first aspect of the present, optionally in a container, and a package insert, package label, instructions or other labelling.

Advantageously, the present invention provides for an antisense oligonucleotide that induces exon skipping of GLDC mRNA, and the use of said antisense oligonucleotide for the treatment of GLDC-expressing cancers.

Those of ordinary skill in the art will appreciate that applications of the above method has wide application for identifying antisense molecules suitable for use in the treatment of many other diseases.

In order that the present invention may be fully understood and readily put into practical effect, there shall now be described by way of non-limitative examples only preferred embodiments of the present invention, the description being with reference to the accompanying illustrative figures.

BRIEF DESCRIPTION OF THE DRAWINGS

This patent application file contains at least one drawing executed in color. Copies of this patent application with color drawing(s) will be provided by the Office upon request and payment of the necessary fee.

The present invention relates to the steric hindrance of antisense oligonucleotides (shAONs) targeting glycine decarboxylase (GLDC) expression. In particular, such shAONs may be used as drug candidates for non-small cell lung carcinoma (NSCLC) and other cancers. The application of shAON to induce nonsense-mediated decay of GLDC mRNA has not been illustrated in previous work. Hence, the present invention may be used to develop novel chemical formulas for a group of highly efficacious (IC50<10 nM) drug candidates against GLDC for NSCLC and other cancers.

EXAMPLE 1

Figure 1:
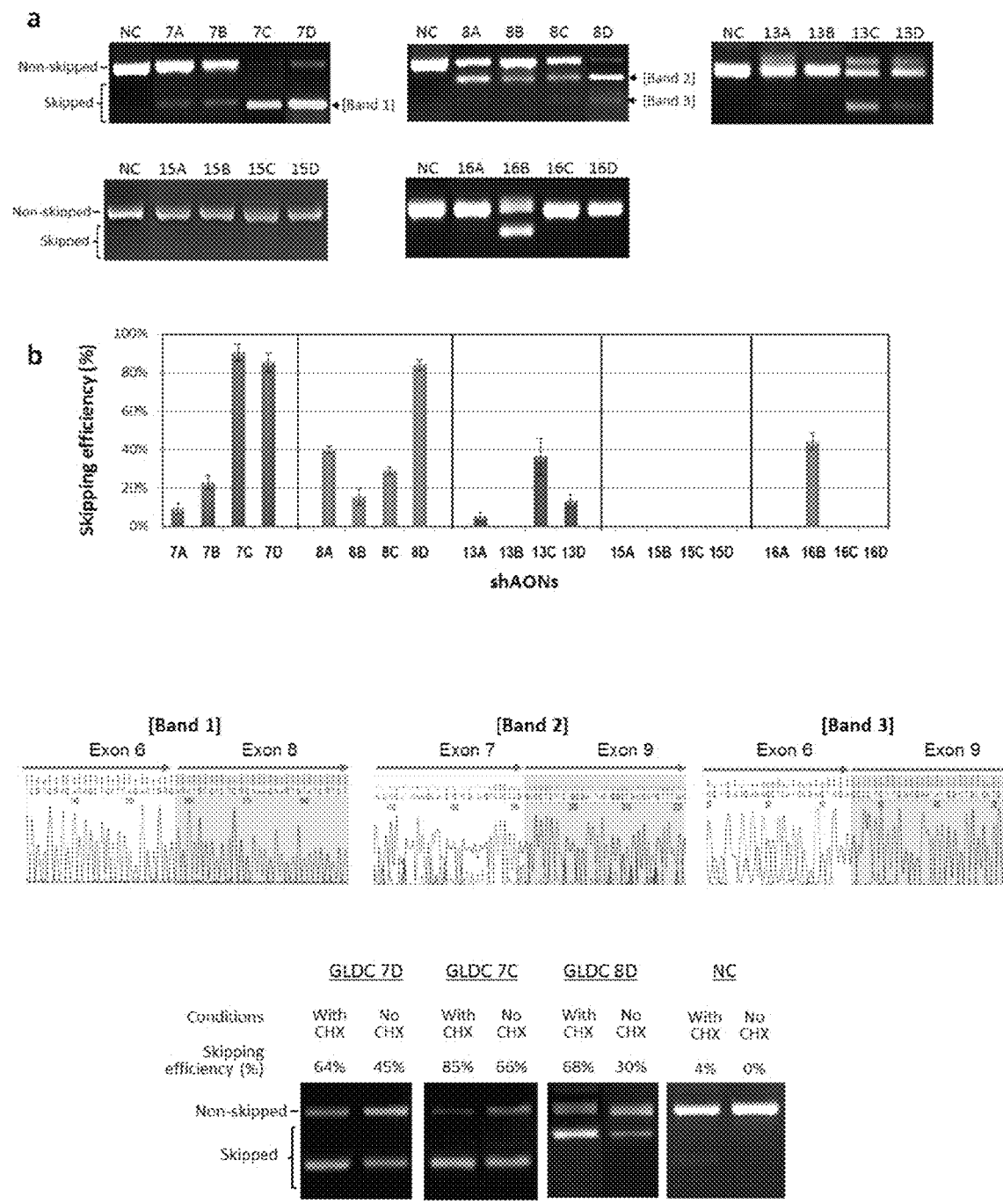
FIG. 1 Selection of shAONs leading to efficient and specific skipping of GLDC target exon. 100 nM of shAONs targeting GLDC were transfected into A549 cells using Lipofectamin 2000. Cells were harvested 16-24 h after transfection and total RNA was extracted and reverse transcribed to cDNA. shAON efficiency in inducing the skipping of the specific target exon was determined by PCR amplification of the region covering the target exon, followed by densitometry analysis of the PCR products. shAON efficiency is presented as a percentage of the amplicons with exon skipping relative to total amplicons. 100 μg/ml of cycloheximide was added into the culturing medium 5 h after transfection to prevent protein synthesis and RNA degradation. a) Images of agarose gel electrophoresis of the PCR products demonstrating specific exon skipping. b) the calculated exon skipping efficiency induced by each shAON. c) DNA sequencing of the bands corresponds to the skipped transcript excised from agarose gel [as indicated in (a)] to confirm skipping of the specific target exon. d) The extent to which the skipped transcripts were degraded by NMD was estimated by shAON transfection under the same conditions as above but in the absence of cycloheximide. Comparison between the skipping efficiency in the two experimental conditions indicate that cycloheximide protects the skipped transcript from NMD, as there is higher proportion of skipped transcript in cycloheximide treated samples.

Here, we have identified 12 novel shAONs (steric hindrance antisense oligonucleotides) that each degrades GLDC (glycine decarboxylase) mRNA as a therapeutic strategy for NSCLC (non-small cell lung carcinoma), FIG. 1 of the attached write-up. GLDC is highly expressed in tumor initiating cells from NSCLC and promotes cellular transformation and tumorigenesis (Zhang et al. Cell 2012; Jain et al. Science 2012); catalytically inactive GLDC is unable to promote cellular transformation. The shAON is a synthetic single-stranded chemically-modified RNA molecule in which every base is modified with 2'-O-methyl linked by phosphorothioate backbones. Each shAON is designed to bind nascent GLDC mRNA complementarily at specific sites and exerts steric hindrance effects against RNA-binding splicing regulators, which are critical for exon recognition and its splicing. Mechanistically, when a shAON induces the exclusion of a specific out-of-frame exon that generates numerous downstream premature termination codons in the mature RNA, the resultant mRNA is targeted for degradation via the nonsense-mediated decay process.

Figure 2:
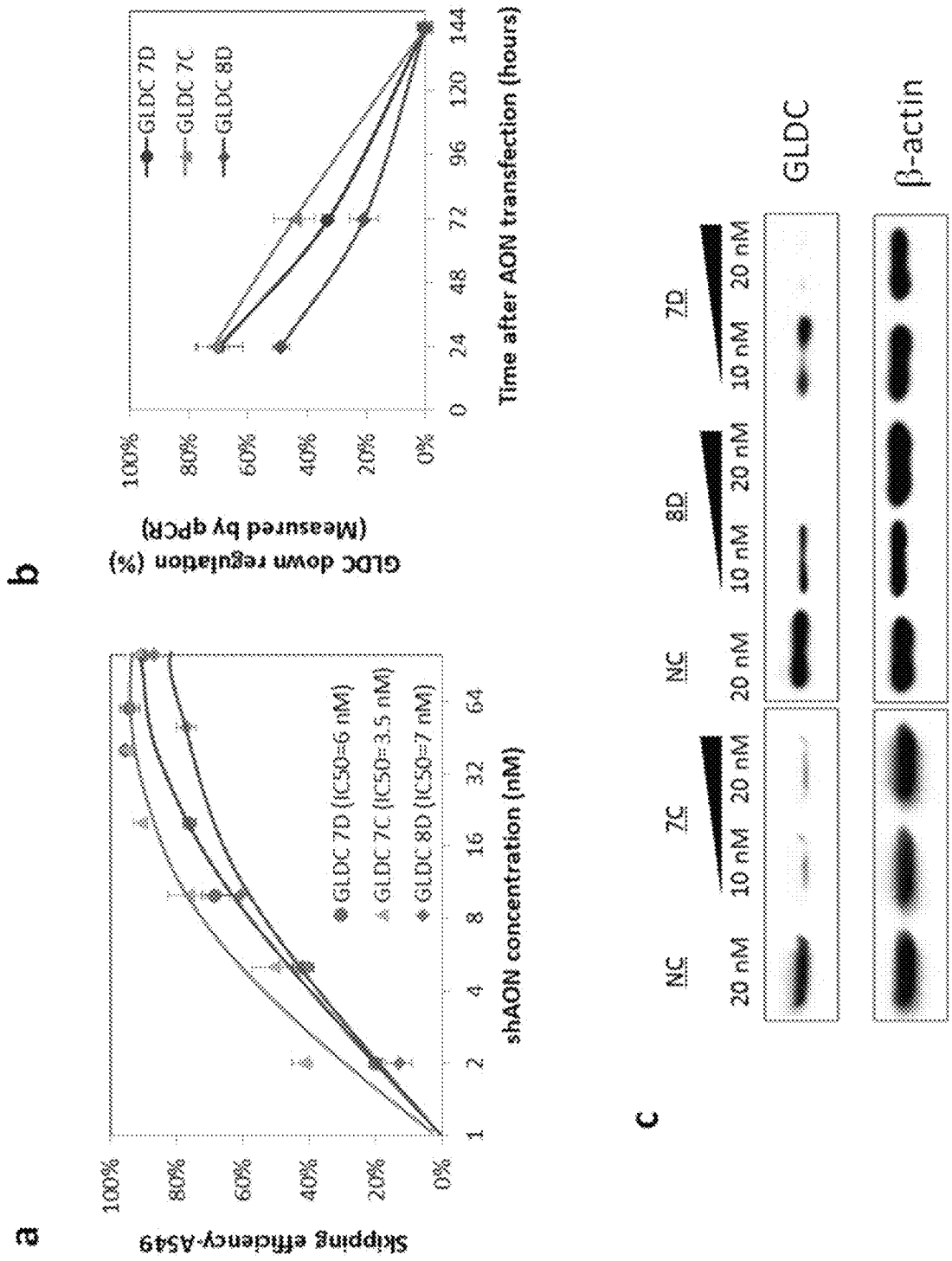
FIG. 2 The 3 selected shAONs induce target exon skipping and inhibit GLDC protein expression at low dose. a) Dose response curves. b) Time course experiment showing the skipping efficiency at different time points up to 144 hours. c) Western blotting of GLDC protein with β-actin as loading control.
Figure 3:
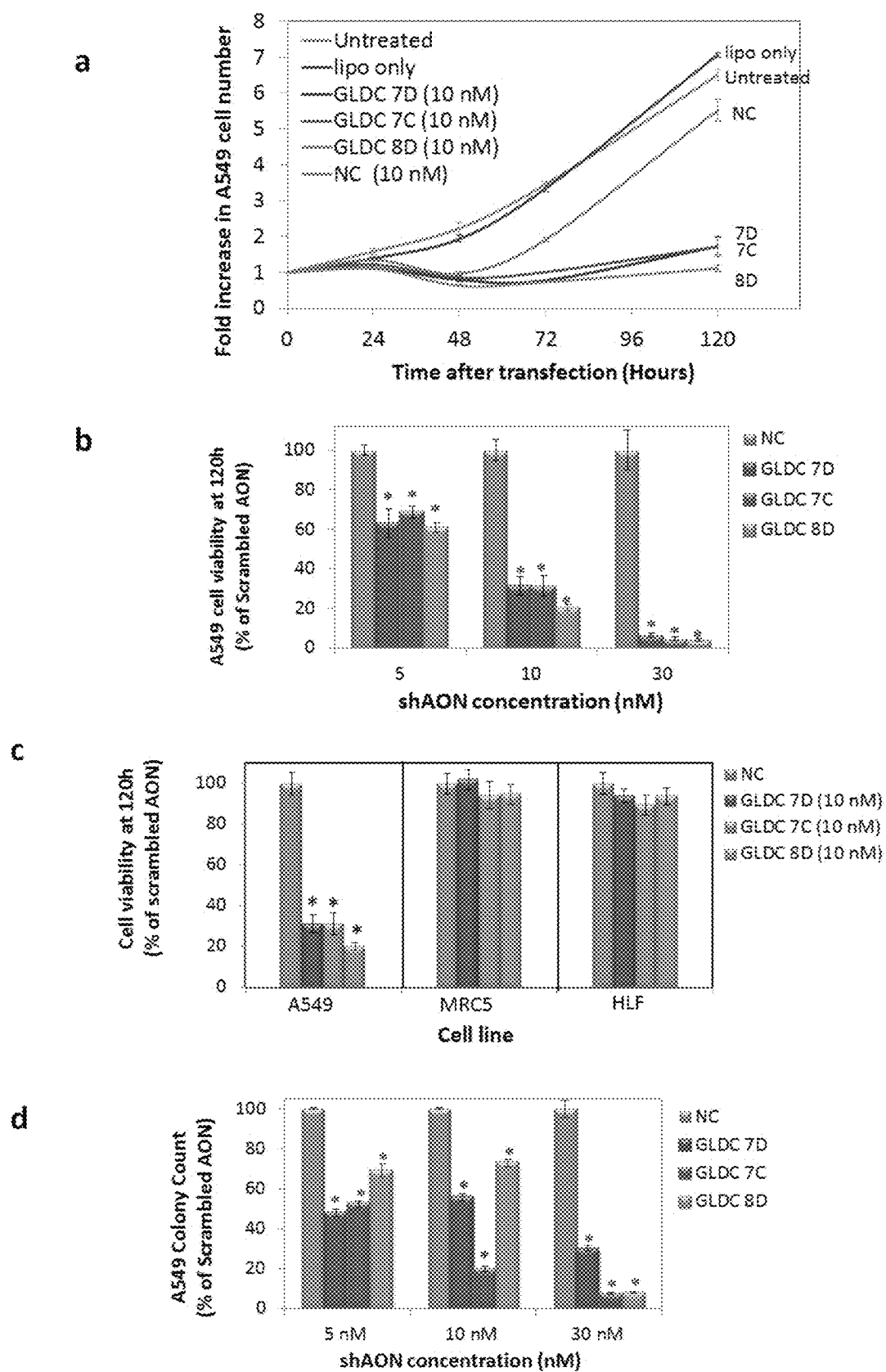
FIG. 3 shAONs inhibit A549 cell growth/proliferation and tumorigenesis. a) Growth curve of A549 cells after shAON transfection at 10 nM; NC—scrambled shAON, lipo only—Lipofectamin 2000 only. b) Effect of various concentrations of shAONs on A549 cell viability at 120 h after transfection. c) Comparison of cell viability between A549, MRC5 and HLF cells at 120 hours after transfected with shAONs 7C, 7D or 8D at 10 nM. d) Soft agar assay of A549 cells transfected with shAON. The number of colonies was counted 7 days after transfection and was normalized with respect to the NC. '*' indicates that the results are significantly different (p<0.01, student's t test) from the scrambled AON control.
Figure 4:
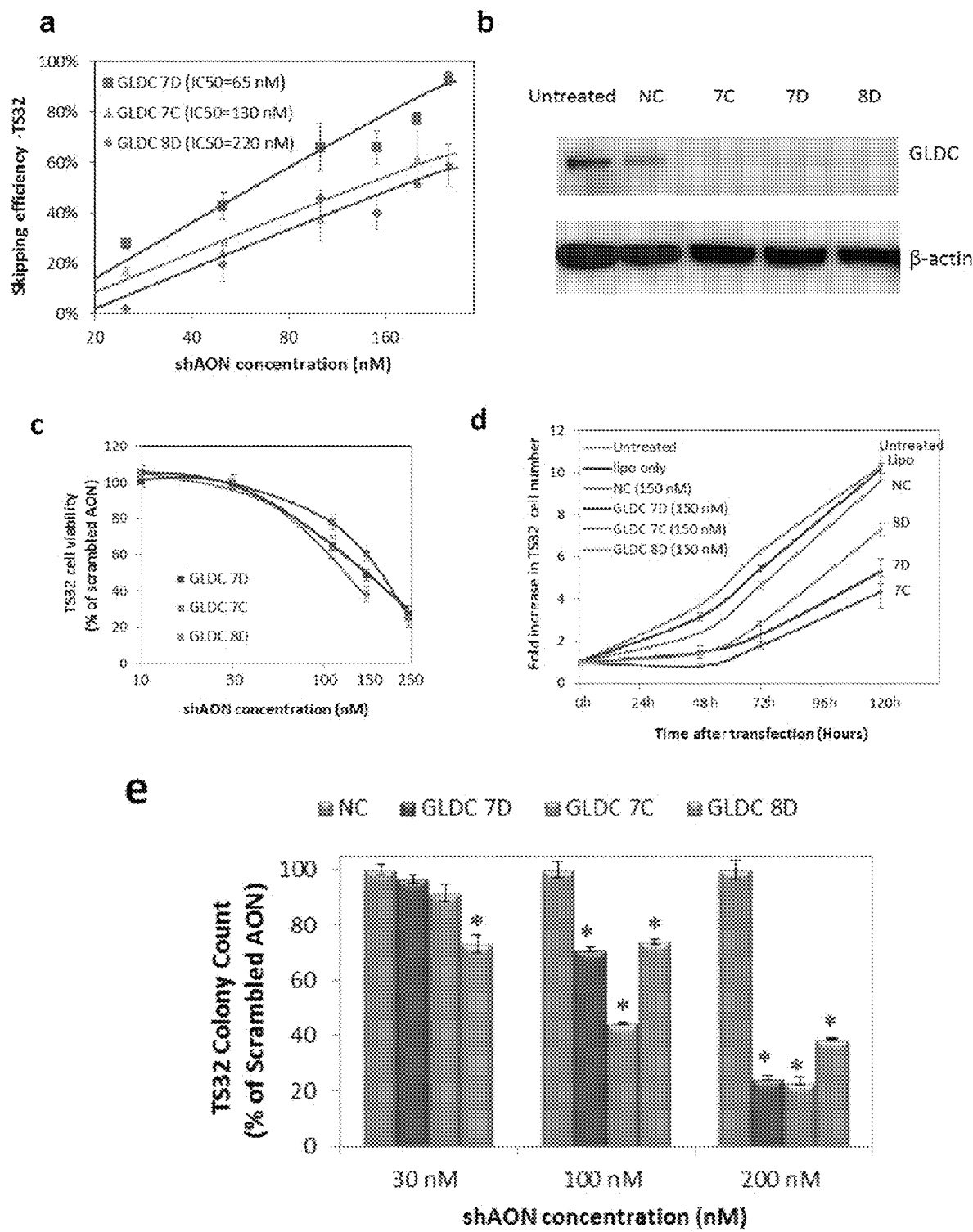
FIG. 4 shAONs induced GLDC knockdown in lung tumor sphere cells inhibited cell growth/proliferation and tumorigenesis. a) Dose response curves of shAON-induced exon skipping efficiency in tumour sphere cells (measured by densitometry analysis). Cells were harvested 24 hours post-transfection. 100 μg/ml cycloheximide was added 5 h after shAON transfection to inhibit the skipped transcripts from undergoing NMD. b) Western blotting of GLDC protein (200 nM) in tumor sphere cells (72 h after transfection) with β-actin as loading control. c) shAON dose response measured using cell viability assay at 72 h after transfection. d) Growth curve of tumour spheres cells transfected with 150 nM of shAONs. e) Soft agar assay for tumor sphere cells transfected with shAON. The number of colonies was counted 7 days after transfection and was normalized with respect to NC samples. '*' indicates that the results are significantly different (p<0.01, student's t test) from the scrambled AON control.
Figure 5:
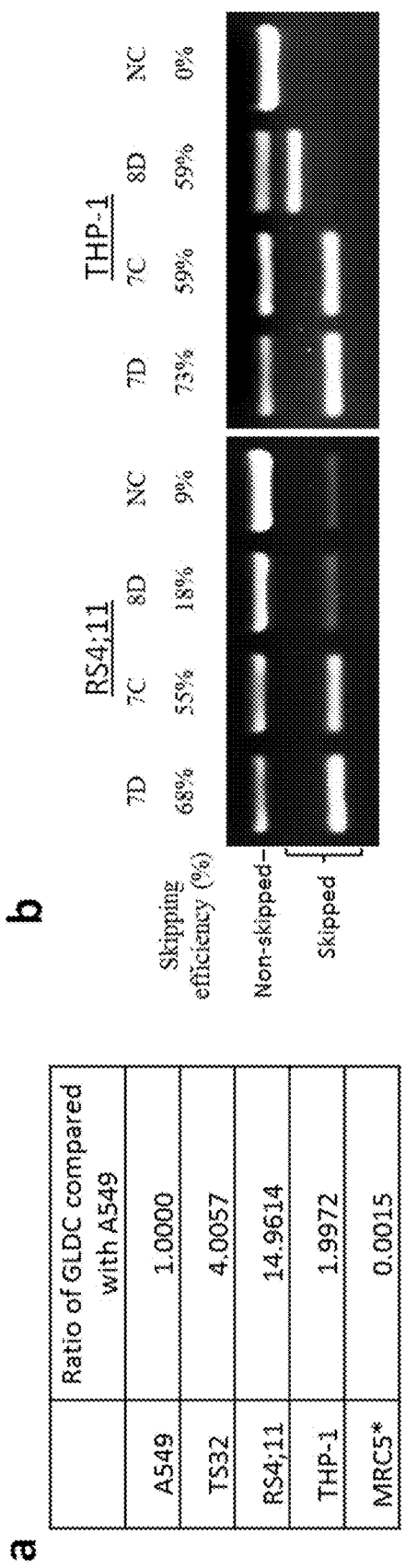
FIG. 5 GLDC shAONs may be effective in inducing GLDC down-regulation in other types of cancers. a) Real time PCR measurement of GLDC expression in different cell lines. b) GLDC shAONs (100 nM) induced exon skipping efficiency in MLL cell lines (with 25 μg/ml cycloheximide added 5 h after shAON transfection).
Figure 6:
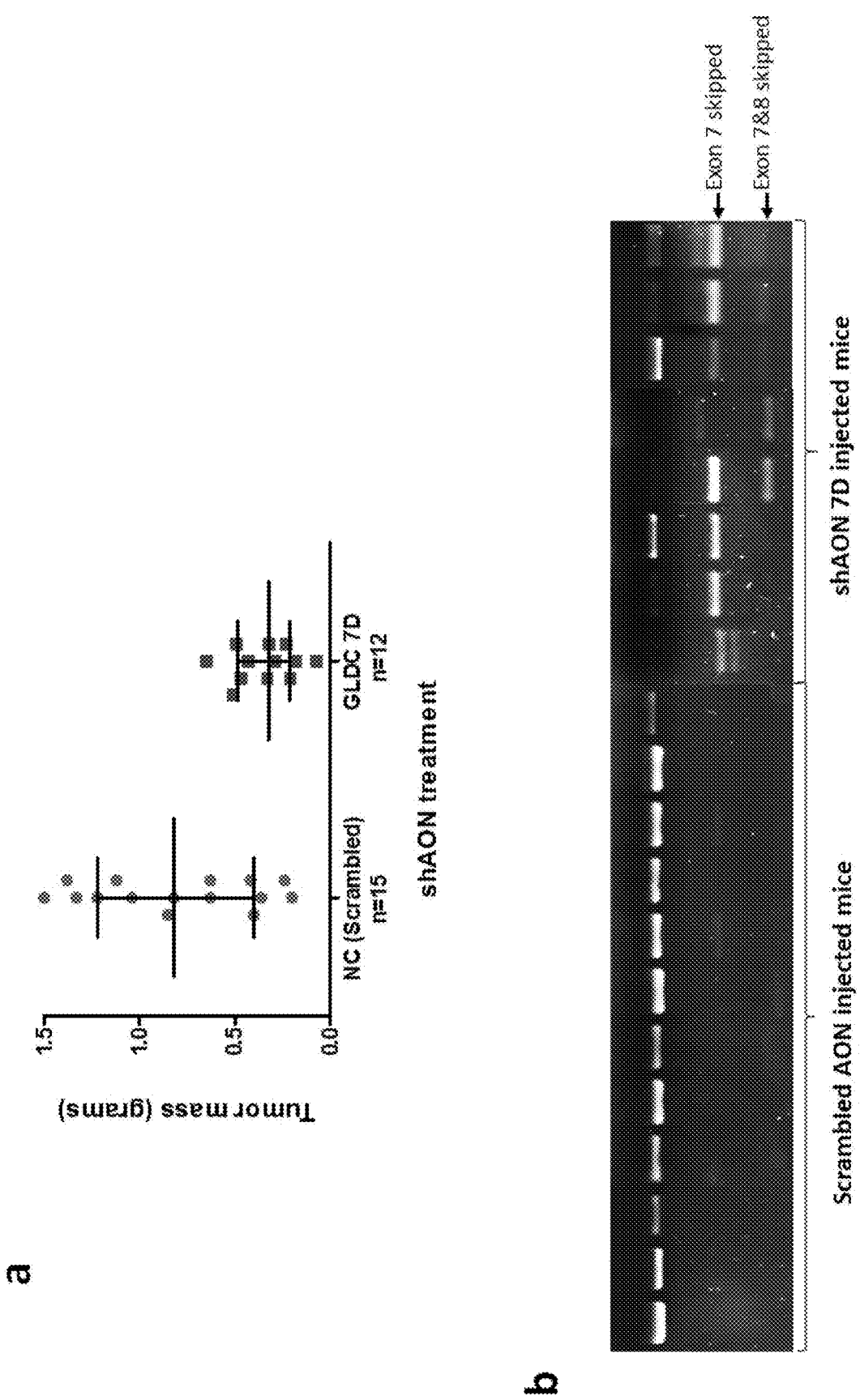
FIG. 6 GLDC shAON induced exon skipping and inhibited tumour growth in human tumor xenografts grown subcutaneously in immune deficient mice. a) Dot plot comparing tumour mass from mice treated with either shAON 7D or NC (Scrambled) (7-8 mice/treatment group). Medians with error bars showing the 25th and 75th percentiles are indicated. The median mass of tumors from 7D treated mice is 60% smaller than from NC treated mice; P-values=0.000676 (unpaired t-sample test) and 0.00391 (unpaired Wilcoxon rank sum test). b) Gel electrophoresis analysis showing exon 7 skipping induced by shAON 7D compared with NC in 20 tumour samples (12 from scrambled control group, 8 from shAON 7D group) extracted from mice. Samples with no detectable PCR products due to RNA degradation are not included in the gel photo.
Figure 7:
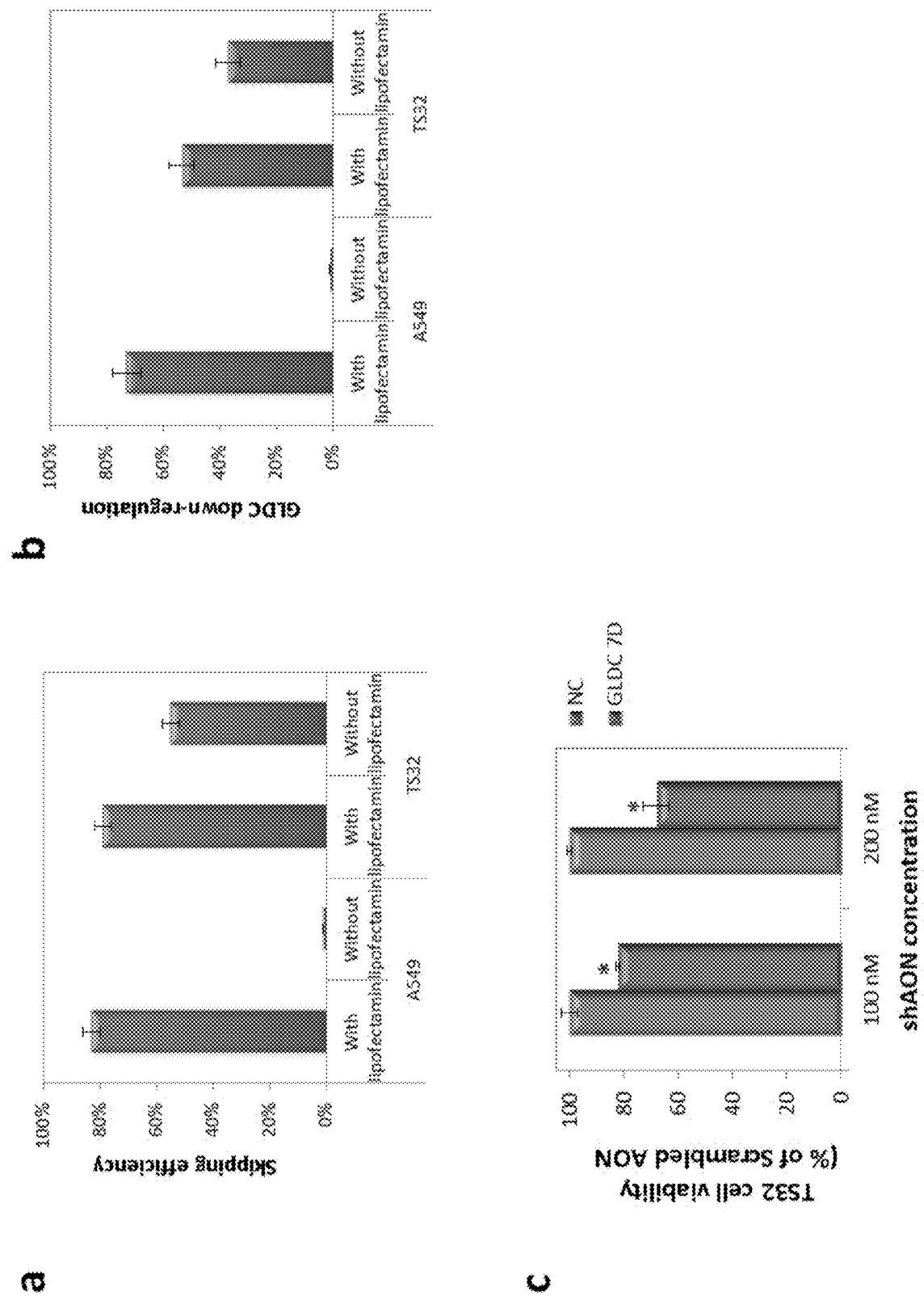
FIG. 7 shAON 7D was able to induce exon skipping, GLDC down regulation and TS32 cell growth inhibition in the absence of transfection agent (Lipofectamin). Comparison of shAON 7D (100 nM) induced specific exon skipping (a) and GLDC transcript down-regulation (b) with or without lipofectamin at 24 h after transfection. (c) Effect of shAON 7D on TS32 cell growth in the absence of lipofectamin at 72 hours post-transfection. In the absence of transfection agent (Lipofectamin), 100 nM concentration of shAON 7D was able to induce exon 7 skipping, GLDC downregulation, and TS32 cell growth inhibition at efficiencies of 55%, 37% and 18%, respectively. The cell growth inhibition increased to 32% when shAON 7D concentration increased to 200 nM.

We select the three most efficient shAONs for further in vitro validation on human cancer cell line and patient's primary cancer cells. In cancer cell lines, each of the shAONs induces specific exon skipping in GLDC mRNA and subsequent suppression of GLDC protein expression with IC50<10 nM (FIG. 2), and inhibits>70% of cancer cell growth (FIG. 3). In primary cancer cells, the shAONs inhibit cell growth/proliferation and tumorigenesis of lung tumor sphere cells (FIG. 4). In addition, the shAONs are efficacious in downregulating GLDC in acute leukemia cell lines (FIG. 5). We further select one shAON for in vivo studies in mice engrafted with lung tumor sphere cells from a NSCLC patient. When shAON is administered systematically via intraperitoneal injection to the engrafted mice, it inhibited 60% of human tumor growth (FIG. 6).

The invention is described in greater detail below.
Material and Methods
Cell Line Culture
Human lung adenocarcinoma epithelial cell line A549 was maintained in DMEM media supplemented with 10% FBS, 2 mML-glutamine, and 1% penicillin-streptomycin. Normal human fetal lung fibroblast MRC-5 cells and human adult lung fibroblasts HLF cells were maintained in DMEM media supplemented with 10% FBS and 1% penicillin-streptomycin.

Tumour Sphere Culture

Tumour sphere TS32 cells were prepared as previously described (Zhang, W C; et al., 2012) and maintained in DMEM/F12 containing ITS (Sigma) and supplemented with 0.4% BSA(Sigma), 20 ng/ml EGF, 4 ng/ml basic fibroblast growth factor (bFGF) (Invitrogen), 1% Penicillin-Streptomycin (Gibco) in non-treated petri dish. Fresh medium was replenished every 3 days. Cells were split with Accutase (EMD-Millipore) to obtain single cell suspensions.

shAON Design and Synthesis shAON was designed using our patented computational method and synthesized by Sigma-Aldrich Pte Ltd (Singapore) modified with 2'-O-methyl of phosphorothioate backbone (2OMePS). shAON with scrambled sequence was included in all experiments.

Cell Transfection with shAONs

Growth medium without antibiotics (i.e. penicillin-streptomycin) was used as transfection medium during cell transfection for all cells/cell lines.

A549 cells were seeded at $1.0$-$1.5 \times 10^5$ cells/wellin 6-well plates containing 1 mL of transfection mediumand incubated for overnight. Cells reached around 40% confluence and the culture medium was reduced to 900 μL before transfection. 10× Transfection mixture with a fixed ratio of 1:2 of shAON (in 100 pmol):lipofectamin 2000 (in μL) at various concentration was prepared in Opti-MEM medium (Invitrogen) to a total volume of 100 μL, incubated for 20 minutes at room temperature, and added into the cell culture.

TS32 cells were seeded at a density of $1.0$-$1.5 \times 10^5$ cells/ml in 24-well plates containing 900 μL of transfection medium. 10× Transfection mixture with various amounts of shAON and a fixed amount of lipofectamin 2000 (5 μL) was prepared in Opti-MEM medium to a total volume of 100 μL, incubated for 20 minutes at room temperature, and added into the cell culture. To ensure reproducibility, transfection was usually done in duplicate or triplicate.

For measurement of shAON induced exon skipping efficiency, cycloheximide (Sigma) was added in the cell medium (100 μg/ml) 5 h after transfection to stop protein synthesis and RNA degradation.

Quantification of shAONs Induced Exon Skipping Efficiency and mRNA Down-Regulation 24 h after transfection with shAONs, cells were harvested and total RNA was extracted using Qiagen RNeasy Mini Kit, treated with DNase (AmbionTurbo DNA-Free kit) to remove contaminating DNA, and transcribed into cDNA using SuperScript™ IIIReverse Transcriptase(Invitrogen) with random hexamer according to manufacturers' instruction.

For measurement of shAON induced exon skipping efficiency, PCR reactions were performed with primers amplifying the region covering the target exon and at least 1 neighbouring exon on both sides. The PCR products were then verified by agarose gel electrophoresis and DNA sequencing to confirm skipping of the specific target exon. Exon skipping efficiency was estimated by densitometry analysis of the gel images by calculating the amount of the targeted exon skip product relative to the total products. Densitometry analysis was performed using ImageJ software (Rasband, W S, ImageJ, U.S. National Institutes of Health, Bethesda, Md., USA).

Quantitative real time-PCR (qPCR) was performed with primers in the targeted exon and outside the targeted exon to measure the amount of full length GLDC transcript using GADPH as endogenous reference in the corresponding samples, and relative to the cells transfected with the same concentration of shAON with scrambled sequence for calculation of skipping efficiency.

Cell Viability Assay

Measurement of cell viability and proliferation was performed in 96 well plate ($3.5 \times 10^3$ cells in 100 µL medium per well) using the Thiazolyl Blue Tetrazolium Bromide (MTT) assay (Sigma) or CellTiter-Blue cell viability assay (Promega). Cells were transfected in the 96 well plate with a mixture of shAON andlipofectamin 2000. For MTT assay (used for adherent cells), medium was replaced by DMEM media (100 µL/well) with MTT (0.5 mg/ml) and incubated for 4 hours at 37° C., and then changed to 100 µL of isopropanol. Absorbance was measured using a microplate reader (Molecular Devices) at a wavelength of 570 nm with background subtraction at 630 nm, and converted to the number of live cells using a calibration curve for absorbance against live cell number. For CellTiter-Blue cell viability assay (for suspension cells), Cell-Titer Blue reagent was added (11 µL/well) and incubated for 4 hours at 37° C. Fluorescence was measured using a microplate reader (Molecular Devices) with an excitation of 570 nm and an emission of 600 nm. To ensure reproducibility, assay was performed at least twice and transfection was done in triplicate wells in each experiment.

Soft Agar Assay 24 hours following shAON transfection, cells were harvested, resuspended with 0.4% of noble agar in DMEM medium, and plated onto 96 well plate ($5 \times 10^3$ cells/well) containing a solidified bottom layer (0.6% noble agar in DMEM medium). Each well was covered with 100 µL of growth medium, and incubated under standard culture conditions for 1 week. Cells were stained with CellTiter Blue and colony counting was performed using a fluorescence microplate reader.

Western-Blotting (Need to Double Check Concentration and Company)

Proteins were extracted from cells using M-PER lysis buffer containing Halt protease inhibitor cocktail with gentle shaking for 10 min at 4 degree. Cell debris was removed by centrifugation at highest speed (12,000 g?) for 20 min at 4 degree and protein concentration of the supernatant was measured using BioRad protein assay according to manufacturer's instruction. 16 µg of protein from each sample was loaded in a 8% Bis-Tris SDS-PAGE gel (Bio-rad) which was prepared according manufacturer's instructions, and then transferred to a Bio-rad nitrocellulose membrane. After blocking with 5% milk in PBST for 1 hour, the membrane was incubated with polyclonal rabbit anti-human GLDC antibody (1:2000) in 3% milk/PBST at 4 degree for overnight, followed by incubation with horseradish peroxidase-conjugated anti-rabbit IgG (1:4000) in 3% milk/PBST for 3 h at room temperature. Beta-actin was used as loading control for western blotting and mouse anti-human beta-actin antibody (1:1000) and horseradish peroxidase-conjugated anti-mouse IgG (1:4000) were used as $1^{st}$ and $2^{nd}$ antibodies, respectively. Visualization was achieved by the ECL system using the Supersignal West Pico chemiluminescent substrate (Thermo Scientific).

Mouse Xenograph Experiment

NOD.Cg-Prkdcscid Il2rgtm1WjI/SzJ mice at 4-6 weeks old were subcutaneously transplanted (500,000 cells/mouse) with single-cell suspensions of tumor spheres in serum-free medium and Matrigel (BD) (1:1). 50 mg/kg dose of shAON was injected intraperitoneally 3 times/week. Mice were sacrificed after 6 weeks of injection and tumors were extracted and weighed. After cell disruption using 0.5 mm glass beads (Sigma-Aldrich) in Micro Smash MS-100 (3×45 s at 4500 rpm), total RNA and proteins were extracted from tumor samples using Qiagen RNeasy Mini Kit and M-PER lysis buffer, respectively.

Results

Selection of shAONs Leading to Efficient and Specific Skipping of GLDC Target Exon Out of the twenty-five exons in GLDC transcript, we selected five out-of-frame exons (exon 7, 8, 13, 15 and 16) as our target for designing shAONs. When each of them is skipped individually, the resultant transcript will have a shifted reading frame downstream of the targeted exon and generate multiple PTCs in the skipped transcript. As a result, the target gene will be either down-regulated via a combination of nonsense-mediated degradation (NMD) pathway wherein the transcript is actively degraded or leading to the translation of a truncated and non-functional gene product. We designed twenty shAONs (4 shAONs/exon) using the computational method which we previously developed and validated. One shAON with a scrambled sequence was included in every experiment as negative control. These shAONs were synthesized with phosphorothioate backbones and 2'-O-methyl ribose modifications (2OMePS) for increased stability and sequence-specificity.

We tested the ability of the designed shAONs to induce specific exon skipping of the GLDC transcript by transfecting A549 human lung adenocarcinoma epithelial cells (FIG. 1) and selected the best shAONs based on the calculated skipping efficiency in inducing GLDC target exon skipping in A549 cells 24 hour post transfection using 100 nM of shAONs. 12 out of the 20 designed shAONs were able to induce skipping of the target exon; Table 1 tabulates the formula of the 12 efficacious shAONs. Overall, shAONs targeting exon 7 and 8 were more efficient in inducing target exon skipping. Three shAONs (7D, 7C, and 8D) were selected as they were able to induce skipping of the target exon in more than 80% of the GLDC transcript.

TABLE 1

| S/No. | shAON Label | shAON formula (5'-3') |
|---|---|---|
| 1 | 8a | UUG UCU CUC CGA AUG UGU UGC UCC CUG GUU |
| 2 | 8b | UGU UGC UCC CUG GUU UGA AGA GCA AGA CG |
| 3 | 8c | GGU AGC CUU GUC UCU CCG AAU GUG UUG C |
| 4 | 8d | UCU CUC CGA AUG UGU UGC UCC CUG GUU UGA |
| 5 | 13a | UGU GAA CAA GGG AAA UGU CUU UAU UUU C |
| 6 | 13c | GUU UCU UCA UGU ACC GGA CAA UGU UUG UUU |
| 7 | 13d | AUG UCU UUA UUU UCC AGU UUC UUC AUG UA |
| 8 | 16b | UUU CUG GUU UAA GUA GGC UCG GAU AGU G |
| 9 | 7a | AGG UGG CCU CAA GAU GCA CAA AGC UAA AAG G |
| 10 | 7b | AUU CUC CAG GUG GCC UCA AGA UGC ACA AAG |
| 11 | 7c | AAG CUA AAA GGU CAG UAG CAC AGC AGG CCA GG |
| 12 | 7d | AAG GUC AGU AGC ACA GCA GGC CAG GCU |

GLDC shAONs Induced Target Exon Skipping and Inhibit GLDC Protein Expression at Low Dose The time and dose response effect of the 3 selected shAON on inducing specific exon skipping in A549 cells was assessed by PCR followed by densitometry analysis. As shown in FIG. 2a, all of the 3 shAONs could induce specific exon skipping at low dose, with $IC_{50}$ ranging from 3.5 to 7 nM. Based on the time course experiment with 10 nM of shAONs (FIG. 2b), their effect on inducing exon skipping decreased with time, but could still induce skipping in >40% of GLDC transcript at 72 hour after transfection.

We performed quantitative real-time PCR (qPCR) to measure the effect of the 3 selected shAON in down-regulating GLDC mRNA transcript in A549 cells. Compared with the cells transfected with the scrambled shAON, the qPCR analysis showed >70% down-regulation of GLDC full length transcript 24 h after transfection with 10 nM of GLDC shAONs. 72 h after transfection, each of the 3 shAONs could still induce >40% down-regulation, consistent with the result from densitometry.

Western blotting analysis was performed to examine the effect of the selected shAONs on GLDC expression at protein level (FIG. 2c). Reduction of protein levels to almost complete depletion was present 72 hours after transfection with 10 or 20 nM of the selected shAONs.

GLDC shAONs Inhibit A549 Cell Growth/Proliferation and Tumoregenesis

Lung cancer cells have been found to be addicted to high level of GLDC (Zhang W C, et al, Cell. 2012 Jan. 20; 148(1-2):259-72). As the shAONs can induce effective knockdown of GLDC when transfected into cells, we therefore tested their effect on cancer cell growth and proliferation. A549 cell viability was measured using MTT assay at 0, 24, 48, 72 and 120 h after transfection with various concentrations of the selected shAONs, and compared with several negative controls including untreated cells, cells transfected with lipofectamin 2000 or the scrambled shAON. The shAON induced GLDC knockdown appeared to inhibit cell proliferation for up to 120 hours after transfection (FIGS. 3a and 3b). Inhibition of cell growth increased from 35% inhibition with 5 nM of shAONs to almost 100% inhibition with 30 nM of shAONs. As shown in FIG. 3c, when transfected with 10 nM of shAONs, growth of two non-cancer cells, HLF and MRC-5 didn't seem to be inhibited while ~70% of cells growth was inhibited in A549 cells.

The shAON transfected A549 cells were then examined for their abilities to form colonies in soft agar, a measure of anchorage-independent growth that typically correlates with tumorigenicity. 7 days after transfection, cells treated with the three GLDC shAONs originated 70-92% less colonies in soft agar compared with cells treated with scrambled shAON, indicating shAON induced GLDC knockdown greatly inhibited cancer cell tumorigenicity.

shAONs Induced GLDC Knockdown in Lung Tumour Sphere Cells Inhibited Cell Growth/Proliferation and Tumoregenesis The cancer stem cells (CSCs) or tumor-initiating cells (TICS), possesses the ability to drive and sustain tumour growth and can be isolated and enriched by sphere formation when grown in in vitro culture. We therefore tested the effect of the GLDC shAONs in affecting growth of tumour sphere cells which are highly enriched for tumour initiating cells. As shown in FIG. 4a, the GLDC shAONs can effectively induce skipping of the specific target exon in GLDC transcripts, with skipping efficiency ranging from 51-93%, and $IC_{50}$ ranging from 65 nM to 220 nM (FIG. 4a). At protein level as measured using western blotting, GLDC protein expression was also effectively inhibited (FIG. 4b). Higher amount of shAONs were required to induce effective exon skipping and GLDC knockdown in tumour sphere cells than in A549 cells.

Compared with tumour sphere cells treated with scrambled shAON, growth/proliferation of GLDC shAON treated cells was inhibited by 57-75%, as measured using CellTiter Blue assay. Soft agar assay also showed that the numbers of colonies formed by GLDC shAONs treated cells were reduced by 61-73% of the colony number formed by scrambled shAON treated cells.

GLDC shAONs may be Effective in Inducing GLDC Down-Regulation in Other Types of Cancers Overexpression of GLDC was not only found in non-small cell lung cancers, but also reported in other types of cancer (Zhang W C, 2012). We evaluated GLDC expression in two MLL leukemia cell lines using qPCR, and confirmed that GLDC was overexpressed in both of them, while the non-cancer cell expressed ~600 times less GLDC (FIG. 5a). We therefore tested if the GLDC shAONs can be effective in these two MLL cell lines. As shown in FIG. 5b, the GLDC shAONs induced skipping of the specific exon in more than 50% of the GLDC transcript in both MLL cell lines, indicating that our designed shAONs may be also effective for other types of cancers.

GLDC shAON Inhibited Growth of Transplanted Tumour

In order to test the effect of shAON 7D in in vivo experiment, we transplanted the tumour sphere cells in immune deficient mice, followed by intraperitoneal injection of shAON 7D. As indicated in FIG. 6, the tumours from 7D and NC treated mice weighted with medians of 0.325 g and 0.820 g, respectively i.e. 60% inhibition of tumor growth (P-value=0.000676 from unpaired t-sample test or 0.00391 from unpaired Wilcoxon rank sum test). RNA analysis of 20 tumour samples (12 and eight from control and shAON 7D groups, respectively) showed that 7D treatment caused GLDC exon 7 or exons 7 and 8 (minor) skipping in all treated tumour samples, whereas almost no GLDC exon skipping was observed in NC treated tumour samples.

Whilst there has been described in the foregoing description preferred embodiments of the present invention, it will be understood by those skilled in the technology concerned that many variations or modifications in details of design or construction may be made without departing from the present invention.

The invention claimed is:

1. A method of inducing exon-skipping of a GLDC pre-mRNA in a GLDC-expressing cancer cell, the method comprising delivering to the cell an antisense oligonucleotide comprising a sequence selected from the group consisting of SEQ ID NOs: 1 to 94, wherein the antisense oligonucleotide is up to 40 nucleotides in length and is capable of inducing exon-skipping of the GLDC pre-mRNA.

2. The method of claim 1, wherein the antisense oligonucleotide comprises a modified polynucleotide backbone.

3. The method of claim 2, wherein the antisense oligonucleotide is modified with 2'-O-methyl and/or 2'-O-methoxyethyl linked by phosphorothioate backbones.

4. The method of claim 1, wherein the antisense oligonucleotide is chemically linked to one or more conjugates that enhance the activity, cellular distribution, target specificity or cellular uptake of the antisense oligonucleotide.

5. The method of claim 1, wherein the antisense oligonucleotide comprises a sequence selected from the group consisting of SEQ ID NOs: 1 to 12.

6. The method of claim 5, wherein the antisense oligonucleotide comprises a sequence selected from SEQ ID NOs 4, 11 and 12.

7. The method of claim 6, wherein the antisense oligonucleotide comprises the sequence SEQ ID NO: 12.

8. The method of claim 1, wherein delivering to the cell of the antisense oligonucleotide results in loss of cell viability.

* * * * *

SEQUENCE LISTING

<160> NUMBER OF SEQ ID NOS: 114

<210> SEQ ID NO 1
<211> LENGTH: 30
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1
uugucucucc gaauguguug cucccugguu                                             30

<210> SEQ ID NO 2
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uguugcuccc ugguuugaag agcaagacg                                              29

<210> SEQ ID NO 3
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gguagccuug ucucuccgaa uguuugc                                                28

<210> SEQ ID NO 4
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ucucuccgaa uguuugcuc ccugguuuga                                              30

<210> SEQ ID NO 5
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ugugaacaag ggaaaugucu uuauuuuc                                               28

<210> SEQ ID NO 6
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
guuucuucau guaccggaca auguuuguuu                                             30

<210> SEQ ID NO 7
<211> LENGTH: 29
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 7
augucuuuau uuuccaguuu cuucaugua                                          29

<210> SEQ ID NO 8
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uuucugguuu aaguaggcuc ggauagug                                           28

<210> SEQ ID NO 9
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
agguggccuc aagaugcaca aagcuaaaag g                                       31

<210> SEQ ID NO 10
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
auucuccagg uggccucaag augcacaaag                                         30

<210> SEQ ID NO 11
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
aagcuaaaag gucaguagca cagcaggcca gg                                      32

<210> SEQ ID NO 12
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
aaggucagua gcacagcagg ccaggcu                                            27

<210> SEQ ID NO 13
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 13
guuggcaggg accgucuucu cgaucaauuc aucaau                                36

<210> SEQ ID NO 14
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uucaaacgga uguuggcagg gaccgucuuc                                      30

<210> SEQ ID NO 15
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ggcaugcaga guugcaagga uuucauuuuc a                                    31

<210> SEQ ID NO 16
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uuuuugcuug aaauggcaug cagaguugca aggauu                               36

<210> SEQ ID NO 17
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ucugguuuuu gcuugaaaug gcaugcagag uu                                   32

<210> SEQ ID NO 18
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
auauacgauc uccagaucug guuuuugcuu ga                                   32

<210> SEQ ID NO 19
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
aguuauaaua gcccaugcca auau    24

<210> SEQ ID NO 20
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cuguggcacu gagcaguuau aaua    24

<210> SEQ ID NO 21
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uccacugaca ucuuuccac ugaaguccau uucacaggg    39

<210> SEQ ID NO 22
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ggguacugga acaacacucc acugacaucu uuuc    34

<210> SEQ ID NO 23
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cuccgugucu ggguacugga acaacacucc acu    33

<210> SEQ ID NO 24
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
aguuccguaa agucuuccac cuuccccucc gugucuggg    39

<210> SEQ ID NO 25
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ugaugagcuc ucuccacgag uuccguaaag                                30

<210> SEQ ID NO 26
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aaagcuaaaa ggucaguagc acagcaggcc aggcu                          35

<210> SEQ ID NO 27
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
caagaugcac aaagcuaaaa ggucaguagc acagca                         36

<210> SEQ ID NO 28
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
agguggccuc aagaugcaca aagcuaaaag guc                            33

<210> SEQ ID NO 29
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
aauucuccag guggccucaa gaugcacaaa gcuaa                          35

<210> SEQ ID NO 30
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ucuaccccaa auucuccagg uggccucaag a                              31

<210> SEQ ID NO 31
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
aaaucucugg gagcugccca gggcgauguc u                    31

<210> SEQ ID NO 32
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
cccccauagc ccaguggcac uccaaaucuc ug                    32

<210> SEQ ID NO 33
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
aaaaaugcug caugggqucc cccauagccc agu                   33

<210> SEQ ID NO 34
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
cggacagcaa aaaugcugc augggqucccc c                    31

<210> SEQ ID NO 35
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
agacgauaca cuucuuuccc aguggcaucu                       30

<210> SEQ ID NO 36
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
cugguuugaa gagcaagacg auacacuucu uuc                   33

<210> SEQ ID NO 37
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
gaauguguug cucccugguu ugaagagcaa gacga       35

<210> SEQ ID NO 38
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
cuugucucuc cgaauguguu gcucccuggu uuga        34

<210> SEQ ID NO 39
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ugguagccuu gucucuccga auguguugcu cccu        34

<210> SEQ ID NO 40
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gauguugcug guagccuugu cucuccgaau guguug      36

<210> SEQ ID NO 41
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
guacagaugu ugcugguagc cuugucucuc cgaaug      36

<210> SEQ ID NO 42
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gaaccauggu agauugcaaa cauggcagc              29

<210> SEQ ID NO 43
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
caaaaucaaa guggcauuau guacccuccu agcaa       35

<210> SEQ ID NO 44
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
augcuggagu ugaugcccug cucgcuugag a                                    31

<210> SEQ ID NO 45
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
caagguauca aagaacaggu caugcuggag uugau                                35

<210> SEQ ID NO 46
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
aaucuucaag guaucaaaga acaggucaug cugg                                 34

<210> SEQ ID NO 47
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
ccuccuucac ugagcagcca cacugaaucu ucaaggua                             38

<210> SEQ ID NO 48
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gaucugccgc ugagcggccc ugcccaagac cuccuuca                             38

<210> SEQ ID NO 49
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ucuugaacac agacccugga auaccucugc a                                    31

<210> SEQ ID NO 50
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ugauggguga ggaacgggcu gguccucuu                                           29

<210> SEQ ID NO 51
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ucauguaccg gacaauguuu guuucagagu gguag                                    35

<210> SEQ ID NO 52
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
aguuucuuca uguaccggac aauguuuguu uc                                       32

<210> SEQ ID NO 53
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uauuuuccag uuucuucaug uaccggacaa uguuug                                   36

<210> SEQ ID NO 54
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
aagggaaaug ucuuuauuuu ccaguuucuu caugua                                   36

<210> SEQ ID NO 55
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
gaacaaggga aaugucuuua uuuuccaguu ucuuca                                   36

```
<210> SEQ ID NO 56
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
ugugaacaag ggaaaugucu uuauuuucca guuu                                      34

<210> SEQ ID NO 57
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
caguggaauc augcugugaa caagggaaau gucuuua                                   37

<210> SEQ ID NO 58
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58 ggggugaug uuugcaaauu cuuccaugu gauagg                                      36

<210> SEQ ID NO 59
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
aaaggggugg auguuugcaa auucuuucca ug                                        32

<210> SEQ ID NO 60
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uccagaggca caaaggggug gauguuugca aa                                        32

<210> SEQ ID NO 61
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
gcugauaucc uugagcuuga uccagaggca caaagg                                    36

<210> SEQ ID NO 62
```

<211> LENGTH: 37
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 62
aaagcugcug auauccuuga gcuugaucca gaggcac        37

<210> SEQ ID NO 63
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 63
aaauccuucu caagcucucg gaaaagcugc ugaua        35

<210> SEQ ID NO 64
<211> LENGTH: 33
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 64
uucacacaaa uccuucucaa gcucucggaa aag        33

<210> SEQ ID NO 65
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 65
ucauaaccug ugaguucaca caaauccuuc        30

<210> SEQ ID NO 66
<211> LENGTH: 37
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 66
gauaguggcc aguccagcau auucucccug ggcuccg        37

<210> SEQ ID NO 67
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 67
aguaggcucg gauaguggcc aguccagcau auucuc        36

<210> SEQ ID NO 68
<211> LENGTH: 36

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
guuuaaguag gcucggauag uggccagucc agcaua                                    36

<210> SEQ ID NO 69
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
cugguuuaag uaggcucgga uaguggccag ucca                                      34

<210> SEQ ID NO 70
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
ucuccuuucu gguuuaagua ggcucggaua gug                                       33

<210> SEQ ID NO 71
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
guucugugcc ccucuccuuu cugguuuaag uaggcu                                    36

<210> SEQ ID NO 72
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
cgagacauca gacccgaagu cuccagggcg acagauu                                   37

<210> SEQ ID NO 73
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
agauuuaggu gcgagacauc agacccgaag uc                                        32

<210> SEQ ID NO 74
<211> LENGTH: 36
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 74
gaaggucuug ugaagauuua ggugcgagac aucaga        36

<210> SEQ ID NO 75
<211> LENGTH: 33
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 75
augcagaagg ucuugugaag auuuaggugc gag        33

<210> SEQ ID NO 76
<211> LENGTH: 33
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 76 cgugggaau gcagaagguc uugugaagau uua        33

<210> SEQ ID NO 77
<211> LENGTH: 31
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 77
cuccuccgug gggaaugcag aaggucuugu g        31

<210> SEQ ID NO 78
<211> LENGTH: 37
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 78
caugccagga ccaccuccuc cgugggaau gcagaag        37

<210> SEQ ID NO 79
<211> LENGTH: 33
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 79
ugggccccau gccaggacca ccuccuccgu ggg        33

<210> SEQ ID NO 80
<211> LENGTH: 31
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 80
gaugauuggg caaaaacggg gcgagauguu u                                    31

<210> SEQ ID NO 81
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81 gcuuaguga aaugacggga ugauugggca aaa                                   33

<210> SEQ ID NO 82
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
auuccgcuuu agugaaauga cgggaugauu                                      30

<210> SEQ ID NO 83
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
aggcauccuc auuccgcuuu agugaaaug                                       29

<210> SEQ ID NO 84
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
acuggagccc caugggggccg cacug                                          25

<210> SEQ ID NO 85
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
ccguggcuug uuuaagaccc uugccuccca ucau                                 34

<210> SEQ ID NO 86
<211> LENGTH: 35
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 86
aucgcaguuu ccguggcuug uuuaagaccc uugcc                                      35

<210> SEQ ID NO 87
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
cauuuaauau cgcaguuucc guggcuuguu uaag                                       34

<210> SEQ ID NO 88
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uguaguuggc auuuaauauc gcaguuuccg u                                          31

<210> SEQ ID NO 89
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ucgcuuggcc auguaguugg cauuuaauau cgcagu                                     36

<210> SEQ ID NO 90
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
uucuaaucgc uuggccaugu aguuggcauu uaauau                                     36

<210> SEQ ID NO 91
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
uguuucuaau cgcuuggcca uguaguuggc auuu                                       34

<210> SEQ ID NO 92
<211> LENGTH: 36
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 92 ucguagugu guuucuaauc gcuuggccau guaguu          36

<210> SEQ ID NO 93
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
aaaagaauuc uguagugugu uucuaaucgc uug          33

<210> SEQ ID NO 94
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
ccugaaaaga auucuguagu guguuucuaa uc          32

<210> SEQ ID NO 95
<211> LENGTH: 79
<212> TYPE: DNA
<213> ORGANISM: Unknown
<220> FEATURE:
<223> OTHER INFORMATION: Description of Unknown:
      Exon 2 sequence

<400> SEQUENCE: 95
agcattgatg aattgatcga gaagacggtc cctgccaaca tccgtttgaa aagacccttg          60
aaaatggaag accctgttt          79

<210> SEQ ID NO 96
<211> LENGTH: 136
<212> TYPE: DNA
<213> ORGANISM: Unknown
<220> FEATURE:
<223> OTHER INFORMATION: Description of Unknown:
      Exon 3 sequence

<400> SEQUENCE: 96
gtgaaaatga atccttgca actctgcatg ccatttcaag caaaaaccag atctggagat          60
cgtatattgg catgggctat tataactgct cagtgccaca gacgattttg cggaacttac          120
tggagaactc aggatg          136

<210> SEQ ID NO 97
<211> LENGTH: 148
<212> TYPE: DNA
<213> ORGANISM: Unknown
<220> FEATURE:
<223> OTHER INFORMATION: Description of Unknown:
      Exon 6 sequence

<400> SEQUENCE: 97
atatactgga gtcctcactg agctgaagtt accctgtgaa atggacttca gtggaaaaga          60
tgtcagtgga gtgttgttcc agtacccaga cacggagggg aaggtggaag actttacgga          120
actcgtggag agagctcatc agagtggg                                          148

<210> SEQ ID NO 98
<211> LENGTH: 197
<212> TYPE: DNA
<213> ORGANISM: Unknown
<220> FEATURE:
<223> OTHER INFORMATION: Description of Unknown:
      Exon 7 sequence

<400> SEQUENCE: 98
agcctggcct gctgtgctac tgaccttta gctttgtgca tcttgaggcc acctggagaa        60
tttggggtag acatcgccct gggcagctcc cagagatttg gagtgccact gggctatggg      120
ggaccccatg cagcattttt tgctgtccga gaaagcttgg tgagaatgat gcctggaaga      180
atggtggggg taacaag                                                     197

<210> SEQ ID NO 99
<211> LENGTH: 97
<212> TYPE: DNA
<213> ORGANISM: Unknown
<220> FEATURE:
<223> OTHER INFORMATION: Description of Unknown:
      Exon 8 sequence

<400> SEQUENCE: 99
agatgccact gggaaagaag tgtatcgtct tgctcttcaa accagggagc aacacattcg        60
gagagacaag gctaccagca acatctgtac agctcag                                97

<210> SEQ ID NO 100
<211> LENGTH: 106
<212> TYPE: DNA
<213> ORGANISM: Unknown
<220> FEATURE:
<223> OTHER INFORMATION: Description of Unknown:
      Exon 9 sequence

<400> SEQUENCE: 100
gccctcttgg cgaatatggc tgccatgttt gcaatctacc atggttccca tgggctggag        60
catattgcta ggagggtaca taatgccact ttgattttgt cagaag                     106

<210> SEQ ID NO 101
<211> LENGTH: 140
<212> TYPE: DNA
<213> ORGANISM: Unknown
<220> FEATURE:
<223> OTHER INFORMATION: Description of Unknown:
      Exon 10 sequence

<400> SEQUENCE: 101
gtctcaagcg agcagggcat caactccagc atgacctgtt ctttgatacc ttgaagattc        60
agtgtggctg ctcagtgaag gaggtcttgg gcagggccgc tcagcggcag atcaattttc      120 ggcttttga ggatggcaca                                                    140

<210> SEQ ID NO 102
<211> LENGTH: 98
<212> TYPE: DNA
<213> ORGANISM: Unknown
<220> FEATURE:
<223> OTHER INFORMATION: Description of Unknown:
      Exon 12 sequence

<400> SEQUENCE: 102

```
gaactggttg ctgaaagcat gggagaggag tgcagaggta ttccagggtc tgtgttcaag    60
aggaccagcc cgttcctcac ccatcaagtg ttcaacag                            98

<210> SEQ ID NO 103
<211> LENGTH: 85
<212> TYPE: DNA
<213> ORGANISM: Unknown
<220> FEATURE:
<223> OTHER INFORMATION: Description of Unknown:
      Exon 13 sequence

<400> SEQUENCE: 103
ctaccactct gaaacaaaca ttgtccggta catgaagaaa ctggaaaata aagacatttc    60
ccttgttcac agcatgattc cactg                                          85

<210> SEQ ID NO 104
<211> LENGTH: 143
<212> TYPE: DNA
<213> ORGANISM: Unknown
<220> FEATURE:
<223> OTHER INFORMATION: Description of Unknown:
      Exon 15 sequence

<400> SEQUENCE: 104
cctatcacat ggaaagaatt tgcaaacatc caccctttg tgcctctgga tcaagctcaa     60
ggatatcagc agcttttccg agagcttgag aaggatttgt gtgaactcac aggttatgac   120
caggtctgtt ccagccaaa cag                                            143

<210> SEQ ID NO 105
<211> LENGTH: 76
<212> TYPE: DNA
<213> ORGANISM: Unknown
<220> FEATURE:
<223> OTHER INFORMATION: Description of Unknown:
      Exon 16 sequence

<400> SEQUENCE: 105
cggagcccag ggagaatatg ctggactggc cactatccga gcctacttaa accagaaagg    60
agaggggcac agaacg                                                    76

<210> SEQ ID NO 106
<211> LENGTH: 113
<212> TYPE: DNA
<213> ORGANISM: Unknown
<220> FEATURE:
<223> OTHER INFORMATION: Description of Unknown:
      Exon 19 sequence

<400> SEQUENCE: 106
gtgggaatct gtcgccctgg agacttcggg tctgatgtct cgcacctaaa tcttcacaag    60
accttctgca ttccccacgg aggaggtggt cctggcatgg ggcccatcgg agt          113

<210> SEQ ID NO 107
<211> LENGTH: 142
<212> TYPE: DNA
<213> ORGANISM: Unknown
<220> FEATURE:
<223> OTHER INFORMATION: Description of Unknown:
      Exon 20 sequence

<400> SEQUENCE: 107
gaagaaacat ctcgccccgt ttttgcccaa tcatcccgtc atttcactaa agcggaatga    60
```

```
ggatgcctgt cctgtgggaa ccgtcagtgc ggccccatgg ggctccagtt ccatcttgcc    120
catttcctgg gcttatatca ag                                             142

<210> SEQ ID NO 108
<211> LENGTH: 112
<212> TYPE: DNA
<213> ORGANISM: Unknown
<220> FEATURE:
<223> OTHER INFORMATION: Description of Unknown:
      Exon 21 sequence

<400> SEQUENCE: 108
atgatgggag gcaagggtct aaacaagcc acggaaactg cgatattaaa tgccaactac      60
atggccaagc gattagaaac acactacaga attcttttca ggggtgcaag ag            112

<210> SEQ ID NO 109
<211> LENGTH: 346
<212> TYPE: DNA
<213> ORGANISM: Unknown
<220> FEATURE:
<223> OTHER INFORMATION: Description of Unknown:
      Intron 6 sequence

<400> SEQUENCE: 109
gtaggtatac ctttcttgtg gggggtccgt ggaggcgtat cccaacttgt atctgtctac     60
ctatctctct ctctgtcttt tcatgtgcct taatttcttt accattatca catggaatgg   120
taaaactctc cttcctgact ccttgctgct actttttttct gttcccggat tcctggcaca  180
tggtgggcac tcagtatgta tttactgaat gaatgaatga gcaatggagt tcacaggatg   240
tgaacacact ctgcccgtct tcctgtagtt aagataattt cctactctcc cactactctc   300
agggaaaggt agcaaccttg ttcctttttct ctcacttcct ttctag                 346

<210> SEQ ID NO 110
<211> LENGTH: 2382
<212> TYPE: DNA
<213> ORGANISM: Unknown
<220> FEATURE:
<223> OTHER INFORMATION: Description of Unknown:
      Intron 7 sequence

<400> SEQUENCE: 110 gtaaagggc tcatgtttct ctactttttat tgtgattatg atttccctga tttcttctga    60
tcacaaatgt tgatttctat ctgaattcaa ctgggccatg ttgagtcagt taaggaaatg   120
tacaacatag attcagaaga acaattctgt ttgggatatg agctagtact tctcaaatac   180
tataaatttg taaatttttg aaaaattttg tgtataattt acaatgtatc gaagtcatgt   240
aacgcatttg cttagattga tggacgcctt gaaagactaa atattttagg catgttttgt   300
gtctcgacag ttttcgttct caaaagcatt atgccacgtg gctctgtaaa gacaaatgca   360
ctgagactgc aaagtacaca ctgagtttgc tccgcgttcc ttcctagagg cttccgccac   420
gtggccattt gagtaatttc caatttccaa atgtactttt cctgactgct tctcattggt   480
gaaacttctc agattaaaaa cgtagatgtt cagaagtagt ctttgttcct taaaaaaaaa   540 agaaagaaa agaaaaaaag ggctgggtgc ggtggctcac acctgtaatc ccagcattct    600
gggaggccga gtcaggcaga tcacaaggtc aggagtccca gacgagcctg gccaatatgg   660 tgaaccctg tctttactaa aaatacaaaa attaggtggg cgtggtggtg ggcgcctgta    720
gtcccagcta cttgggaggc agaggcagga gaatcacttg aaccacgag gtggaggttg    780
```

```
cagtgagccg agatcgcgct gcctcactcc agtttgggtg cagagcgaga ctccatctca    840
aaaaaaaaaa agaaaaaaaa ggaaaaaaaa ggagcggggg acctagatgc attccaggat    900
tattactggg gaaatttaga aaaaaaaatt atgttttga cctttgataa aagctggact     960
ttaacataag tgagtaagct gaattagtca atgatgtgat gataatgtga agtgtgtttt   1020
tttaaaattt tatttattta tttatttatt tattttgaga ccaagtctca ctccatcacc   1080
caggctggag tgcagtggtg taaacgtggc cactgtgtcc aactaatttt ttaaattttt   1140
tgtaaaaaca gggtttcacc atattgctca ggctggtctt agggctcaag tgatctgccc   1200
accccagcct cccaaaatgc tcggattacc aggtgtaagc caccatgcct ggcctctgta   1260
tactttaaat catcttatta acacctaatg ttatgcaatg gttgttacac tgtattgttt   1320
ttaaaaattt gtgtgatttg ttttttttt tttattttt gagacggagt ctctctctgt     1380
cacccaggct ggagtgcagt ggtacgatct tggctcactg caacctctgc ctcccaggtt   1440
caagtgattc ttgagcctca gcctcccaag taactgagat tacaggtgcc tgtcaccatg   1500
tctggctaat ttttgtattt ttagtagaga tggggtttca ccatgttggc caggctggtc   1560
tcaaactctg gacctcaggt gatccgccca ccttggcccc ccaaagtgct gggattatag   1620
acatgagcca ccatgcgcgg ctcataaaat ttgtgtgatt tttaattgtt gtattatttt   1680 ttatttttt gaatgttttc agtccgtgat tggtggaatc tgtggtgtag aatccacaga    1740
gagccaagtc ttttcaattt tgtcgtatat ttccactttt cctgtgtctc ctaagaagtt   1800
cagagtgaaa cttaatcctc ccagtcacca ttattgtatt tgtctgggaa attcctgcaa   1860
aattttcttt caaaattcct agacttattg tatatatctt ggtgtctcag agtacagtct   1920
aaaaatcagt aatcctgctg ggcacagtgg ctcatgcctg taatcccagc actttgggag   1980
gccaaggcag gcggatcacc tgaggccagg agttcaagac cagcctggcc aacatggtga   2040 aacccccatct ctactaaaaa tacaaaaatt agctgggcgt ggtgtcagga ggctgatgca   2100
gtagaatcgt ttgaaaccag aaggcagagg ttgcagtgag ccgagatcac gccattgcac   2160
tccagcctgg gcgaaagagc gaaactccgt ctcaaaaaaa aaaaaaaaa tcagtaatca   2220 tgtttagatg aggaacgttt agaaattgtt tcttttataaa tttgcaccca agtgcatttg   2280
ctgaattcac ttcaagctgg gaaggaaaga agtaattcta tttatagcat ctcccagtgc   2340
tgtgattatc tgtgctaact ggatgcctta ttcttggtgt ag                      2382
```

<210> SEQ ID NO 111
<211> LENGTH: 6989
<212> TYPE: DNA
<213> ORGANISM: Unknown
<220> FEATURE:
<223> OTHER INFORMATION: Description of Unknown:
      Intron 8 sequence

<400> SEQUENCE: 111

```
gtaaatcaca cgtctgacct gactactgaa tgccttacga tacacagaaa tgagctactc     60
attcattcat tcatttgttc atttattcac cacctcctga gcagtgagca caccagaaat    120
ggcaagatct tattggtgta aaggctcat tgtcttatga aaccaaaat acagtattgg      180 ctgggtacgg tggctcatgc ctgtaatccc agcaccttgt gaggccaagg caggcagatt    240
gctggagccc aggagttgga aacctgcctg ggcgacatgg cgaaacacca tctctatgaa    300
aaataaaata aaataaatta gccgtcagtg gtggtatgct cctgtagtcc caggtgctag    360
ggaggctcag gtgggaggat caccagaatc tgggaggttg aggctgcagt gagccatgat    420
```

-continued

```
tatgccactg cactccagcc tgagtgacag agggagactc tgtccccaac tcctgccccc      480
acaaaaaaag ttaaagaaaa agacactgtg ttttactggt gttctttata tgtacaccat      540
ttgcctatgc tttctcttca ccatacatgt tttaatacta aaaaaaataa aaagcattat      600
ttgtttcatt ttacccataa tcacatcttc agatcctgaa caggcaaagc gtaagaaagg      660
acaaaaaagg ccagtcttca cttttatata cagacttaaa atatatgtaa atagaaagat      720
ggatatcagg gtctctagta ttcttggcgt tgggccaggt ttgttatggg tggcagttga      780
gacaccctct cttaggactg agaaggagcc tctccaggaa tgggttgagg aaggcaaagc      840
aagggcattt gtgatgactg tgcttgaggg gatggtggta gtcatgaggc actcttactg      900
ggagattatg actggcattc ttttttttgt ttttcgaga cagagtttta ctctgtcgcc      960
caggctggag tgcagtggcg caatctcagc tcactgcaac ctctgctgcc cggtttcaag     1020
caattctcct gcctcagcct cctgagtaac tgggattaca ggcgcctgcc acagcgccag     1080
gctagttttt gcattttttag tagagacggg gtttcaccat cttggccagg ttggtcttga     1140
actcctgacc tcatgatcca cccacctcgg cctcccaaag tgttgggatt acaagcatga     1200
gccactgcac ctggccatgt ctggcattct ttaaaaggat gggataaaac aggaagagct     1260
tcctgggttc tgaccagggt tctgggttct gctccttgaa gttgctccag ggcttaggtc     1320
gaagtgtttg tgaaacccag ccaaacccta ggatcagttg gaggcccact cctgagcaca     1380
ggatccattc taagtgcatc tcttttttt ttcttcttc tttttttttc ttctttgaga      1440
tagagtcctg ttcctgcgtc acccaggttg gaatggggtg gcgcaatctt ggctcactgc     1500
aacctctgcc tcctgggttc aagtgattct tgtgcctcag cctcctaaag agctggaatt     1560
acaggccacc acacccagat aatttttgta tttttagtag aggcaggttt catcatgttg     1620
gccaggctgc tctcaaacgc ctgacctcaa gtgatggtcc tgcctgggcc tcccaaaatt     1680
ttgggattgt aggtgtgagc catggcacct ggcttctttt ttttttttt tcttgagaca     1740 gattcttgct ctgttgtcca ttctggagtg cagtggcatg ccatagctc actgcagcct     1800 caaccttcaa cctccagggc tcaaattatt ctccggtctc agcctcctaa gtagctggga     1860
ctatgggtac attccaccac gcccagctaa ttttcaaaaa aatgttttgt agaggcgagg     1920
tctcactttg ttgctcaggt tggtctcaaa ttcctgagct caagtgatcc tatccttggcc    1980 tcccatagtg ataggattat aggcatgagc caccgtgcct ggccactgta attgcatctc     2040
ttccatgaag tgtcagagag agatgtcaca ggtgcttcaa tgggaggtag agtgctcttt     2100
cgtctcaggg ctttggcgtc tagaaccacc tctgaaaagc ttctccagga aggcagtggg     2160
caataagatc ttcttatagt tggttctgca gccacgggtc tttggagcca tttcctcagt     2220 tggtccttt gtattatgtt ttgcctcagg aaggtgccac ctcttttcaa atatgagctc     2280
ttccagtatg ataggaagga aaggtggttg gcacaggctt ttcctctgtt gaacagcaag     2340
ctgatcttta tttatttatt tgtttttttg gttgtttttt tttttttga gatggagtct     2400 tgctctgtca cccaggctgg catgcagcgg cccaatctca gctcactgca acctctgcct     2460
tccagtttcc agcgattctc ttgcctcagc ctcctgagta gctgggatta caggcgcctg     2520
ccaccatgcc caactaattt ttctattttt agtagagaca gggtttcacc atgttggtca     2580
ggctggtctc gaactcctga tctcatgatc tgcccacctc ggcctcccaa agtgctggga     2640
ttacaggcat aagccgccat gcctggccac atggtgatct ttatatggtg gcctcacttt     2700
ctgtagctta ccctccattt gttgaattct ctgcttacgt tttcccttc ggtgcagctg      2760 actgctcctg tcttgctgtt tctcctcagg ttcctccagg tttccgtctg atcataagtc     2820
```

```
catttagggc ctcagttttc tgcctctagg ttcattttcc aggtgaattt gggctgtctg   2880
cagtgaacca gttatgttcc tgtttctttc tttttttttt ttttgagacg gagtctttct   2940
cttgttgccc aggctggagt gcaatggcgt gatgtcggct cactgcaacc tccgtcttcc   3000
gggttcaagc gatactcctg cctcagcctc ctgagtagct gggattacag gcacccacga   3060
ccatgcctgg ctaatatttt ttgtattttt agtagagatg gggtttcacc atgctggcca   3120
ggctggtctc gaactcctga cctcaggtga tccgcccgcc ttggcctccc aaagtgctgg   3180
gattacaggc atgagccatt gtcccggcc ttatgttcct gttgcttaat ttcttccagt   3240
tcatgtatag ctgataattt attatttaac ttgggttgaa aggtctgtat cttttccagc   3300
aattgttaaa atgtttgccc tggagatggc catactccag cttgtctgat tttcatcctc   3360
ttattctgat gatcttctaa ctcttcactg tctatttcac tgcatatgtg ccttttcata   3420
gttgattgca tacaagaatt actcataact ccagtttcac tctttgtgag catgcaagtc   3480
tccctgtttt gttaggagat gactggtgtc ttttgagttg ttccttttgt gctgtaggtc   3540
tttgaccccc gccttctgtt gtagcagctg ttccacattc ttctcactct gctcttctc   3600 tcttgtcact ggggtgggtg ggggagtcca ctcttagttt cgcatcgtgg atggggcatg   3660 actcttttt aatctctgaa agtgtgttaa tgattctttt ttaaataaat ttttctatag   3720
ggagtctctc tgagcctatt ctggctcagc aggccccatt ctaaaacaaa actgaaaaaa   3780
cagggtgcgg tggctcacac ctgtaatctc aacactttag gaggccaagg caggaggatt   3840
acttgagttc agcagtttaa atccatccca ggcaacatag tgagactcct gtctatataa   3900
aaaaagtaca aaaattagcc aggtgttgtg gtacacacca gtatcccagc tactcagtag   3960
actgaggtgg taggagtgct tgagctgggg aggtccaggc tgcagtgagc tgcaatcaca   4020
ccactgcact ccaacctggg tgacagaatc agaccccacc tctacaaaac aaaaaggaaa   4080
agaaacaatt ttttctataa atttgtggca ttactacaga tgtctgaatt ttcattatgt   4140
tctgttcttt atattctctt atttcttttt tttttggaga cgagtctcgc tccatcgccc   4200
aggctggagt gcagtagcgc catctcgctc actgaagctc tgcctcccgg gttcacgcca   4260
ttctcctgcc tcagcctcct gtgtagctgg gactacaggt gtctgctacc atgcctggct   4320
aatttattgt attttagta gatacagggt ttcaccatgt tagccaggat ggtctcgatc   4380
tcctgacctc atgatccacc tgcctcagcc tcccaaagtg ctgggattac aggcgttagc   4440
caccatgccc ggccatatat tctcttattt cttagcttct accacaatga gcagctcttt   4500
cattggcttt tcttattttt aatataaaaa tcttttttaaa atagagatgg gagtcttact   4560
ttgttgccca ggctagtatt gatctccagg cctcaagcga tcctcctgcc tcagcctccc   4620
aaagtgttgg gatcactggt gtgagccact gcatccagcc ttgttggctt ttctaaagtc   4680
aggtgtagta aagaataatt tacactttat tagcttttttt tattgagatg taactcaccg   4740
taagtttcac caattgcaag tatacagctc aatggttttt actctattta caaggttgtg   4800
caactatcac cagtatttaa tttcagaata ttttttattac cccaaaaaga aattctattc   4860
ctatgaagta gtcactcctc atccctctcc ccttcctata gccccctggca actactattc   4920 tactttctgt ctccctggat ttgcctgttc tgaatatttc atataaatgg gatcatacaa   4980
tgtgtggcct tttgtacctg gcttctttgc ataaggtttt caaggttcat ccatattgta   5040
gcatgaatgt gtacttaatt cttttctatg gctgggtaat atcccattgt ttggacatgc   5100
tacattttgt ttatccattc atcaattggt aaacatttgg ggtgtttcaa ataagcctgc   5160
```

-continued

```
tgtgaacact tctgtgtaaa tttttgtatg gatgtaatgt tttcagttct tttggttata      5220
ttcctagcag tgaaattgct gggtcatata actctacatt taacattttg aggaacttcc      5280
agacattttt caaagtggct gcattatttt actttcctac cagcagcata tgaatattct      5340
aatttctccg tattttcacc aatgcttgtt acttcctatc ctttggttat agccatccta      5400
ttggatgtca agtgataatc tcactgtggt tttgttttgt atttccctaa taactaatga      5460
ttttgagcat tcattagctt ttgaggcttt taagtacctt aattgtatta ttgttatttt      5520
atttatttat tttagagatg gggtcttgtt atgttcttct tgctggtctt taactcctgg      5580
gctaaagcaa tcctcccacc ttagcctccc aaagtcttgg gattacaggc gtgagccact      5640
gattcaagcc ctttgtattt ttaagtttgt tcaatttgtg aaagaaattg tcattttctt      5700
ggtctctatt ttaatttttt tggttcttct tttgatattc tagtgccctt tgaagttttt      5760
aaaaagtggt tttatacttc tcatcaattt gttgttcagc cgtgtgatat agcctcctga      5820
ttatggaagg aatcatctgt agattaaaaa gggacatgaa ccaacctcta caatattgtg      5880
gtggaggctg ccagggcatt ctgtgaatgt caggcctggg tttctgtttc cagcaacaca      5940
gccatgagca tttgggcaca gtgtgtcaca gattctttac ctcagcctcg ccttttccac      6000
agctgtaaag tgctgtggag ttttctgtgtt tatttctgat tgttgtaagg agtccataag      6060
agtgtttaca ctttgtctag acttttagt acaagaatgc ctacttccat gttttctgat      6120 gtctcttttct cctcatttac ttccttgttt gctgacttca cctttggaaa ctgtttctta      6180
ttttgcattg gctccataga gacttcctct agtagtctag cagaaaaaaa gatgtaccta      6240
acaaaatgga cccagtattg aacatcaact gtattttgca gagacagggt tttgtattgt      6300
caaccgggct ggagtccagt ggcgcaatca taggtcactg taacctcgaa atcctgggtt      6360
caagtgatcc atctcggctt ctggagtcac tgggactaca gttgcacacc accccgctcc      6420
cagctgaagt gcgcattgcc gttttttgcca gtcctttgcc acagattctc cattcaactc      6480
ttggttggca gaagttcagc ctctagtgtt ttatttaagt tcttaggaga attttattcc      6540
tgaagttctt gaatgtttga aaattgcttg tttctttta ttcttgaaga attgcctggt      6600
tgagtgtaaa attctcagat ctcactttt ctccctgagg tctttattgc ttcactgtct      6660
tccaacatta acattgctt ctcaatgtct gatggtagtg tgatctttgc ccttaagggt      6720
gacatgattt tgttgcatgg aagaagccct tcgtaatggt caaatgtgaa ggtttagtat      6780
agtaacaact ccagggtgtc ttggatgatg gttcctttca ggtagtcagg caggttatat      6840
attaattgtc cccaactatc aaagaatgta ggaaatctga tcattttgtt ttgtcgctgt      6900
cttcagtttt gacatcccaa gtcaagtaat tacaccctcc cactaattgt cctccatcac      6960
gtgattcttt aaatgttctt atcttttag                                       6989
```

<210> SEQ ID NO 112
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 112

```
cgtggagaga gctcatcaga gtgggagatg ccactgggaa agaagtgtat cgtct           55
```

<210> SEQ ID NO 113
<211> LENGTH: 54
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 113
agcccgaaga aggggggtaa caaggccctc tcgcgatatg gctgccatgt ttgc          54

<210> SEQ ID NO 114
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
cgtggagaga gctcatcaga gtgggccct cttggcgaat atggctgcca tgtt           54
```